(12) United States Patent
Richards et al.

(10) Patent No.: US 11,107,560 B1
(45) Date of Patent: Aug. 31, 2021

(54) METHODS, SYSTEMS AND APPARATUS FOR PROCESSING AND DISPLAYING COMMUNITY PATIENT DATA ALONGSIDE NATIVE PATIENT DATA

(71) Applicant: ALLSCRIPTS SOFTWARE, LLC, Chicago, IL (US)

(72) Inventors: Michael Andrew Richards, Jericho, VT (US); Alan Raymond Ouellette, Stowe, VT (US); Christine Marie Mariani, Homer Glen, IL (US); Kevin Urie Frey, Bristol, VT (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 933 days.

(21) Appl. No.: 15/368,566

(22) Filed: Dec. 2, 2016

(51) Int. Cl.
  *G16H 10/60* (2018.01)
(52) U.S. Cl.
  CPC ................... *G16H 10/60* (2018.01)
(58) Field of Classification Search
  CPC ....................................................... G16H 10/60
  USPC ........................................................ 705/2–3
  See application file for complete search history.

(56) References Cited

U.S. PATENT DOCUMENTS

| | | | | | |
|---|---|---|---|---|---|
| 6,038,231 | A * | 3/2000 | Dolby | ................. | H04L 12/5602 370/394 |
| 7,802,206 | B1 * | 9/2010 | Davis | ............. | H04M 1/274525 715/864 |
| 2009/0150176 | A1 * | 6/2009 | Gejdos | ................... | G16H 10/60 705/2 |
| 2012/0215560 | A1 * | 8/2012 | Ofek | ..................... | G06Q 10/10 705/3 |
| 2013/0046558 | A1 * | 2/2013 | Landi | .................... | G06Q 50/24 705/3 |
| 2015/0379241 | A1 * | 12/2015 | Furst | ..................... | G06F 40/247 705/3 |
| 2016/0357932 | A1 * | 12/2016 | Morris | ................... | G16H 50/30 |
| 2018/0121606 | A1 * | 5/2018 | Allen | .................... | G06F 19/326 |

OTHER PUBLICATIONS

School of Data, "Web APIs for non-programmers", Published Nov. 2013 (Earliest record in 2014 via WayBack Machine), https://schoolofdata.org/2013/11/18/web-apis-for-non-programmers/ (Year: 2014).*
Marriam-Webster, "Standardize," 2009 (Year: 2009).*

* cited by examiner

*Primary Examiner* — Jason S Tiedeman
*Assistant Examiner* — Rachel F Durnin
(74) *Attorney, Agent, or Firm* — Loza & Loza, LLP; Peter Zura

(57) ABSTRACT

A method for facilitating integration of patient electronic healthcare record information from a community aggregator with electronic healthcare record information native to an electronic healthcare record (EHR) application includes, for each of a plurality of accessed community data items, comparing the community data item to native data items, and based on the comparison, identifying the community data item as a duplicate, a potential duplicate, or not a duplicate, and for each community data item which was not identified as a duplicate, comparing the community data item to entries in one or more native clinical dictionaries, and, based on the comparison, identifying the community data item as an exact match to a clinical dictionary entry, a potential match to one or more clinical dictionary entries, or not matched to any clinical dictionary entry.

20 Claims, 32 Drawing Sheets

*Prior Art*

| Smith, Sa | Search | 🔊 Rx ⊞ ⊟ ⊕ |
|---|---|---|

Please select a patient...

☺ Smith, Sally A.
Age: 31 | Sex F | MRN 933145526

☺ Smith, Sally A.
Age: 64 | Sex F | MRN 954145327

☺ Smith, Sam P.
Age: 73 | Sex M | MRN 933145526

☺ Smith, Sandra C.
Age: 12 | Sex F | MRN 997153218

☺ Smith, Sandra F.
Age: 59 | Sex F | MRN 642343578

☺ Smith, Sasha J.
Age: 22 | Sex F | MRN 974133225

1001
User selection of a patient in EHR Web App represents new patient context

*FIG. 2*

*Prior Art*

| Smith, Sam P. | | | | Search | |
|---|---|---|---|---|---|
| Age: 73 | Sex M | MRN 933145526 | | | | |
| Problems | Immunizations | Meds | Allergies | Orders | Patient Worklist | Chart Viewer |

Active Problems ▽  Type ▽

| Name | ICD-10 | Managed By | Last Assessed |
|---|---|---|---|
| Problems | | | |
| Asthma | J45.909 | Dr. Leonard Spock (Cardiac) | 09 Oct 2016 |
| Migraine Headache | G43.909 | Dr. William Kirk (Internal Medicine) | 13 Sep 2016 |

DUR Alerts:  Drug-Drug (0)   PAR (0)   Disease (0)   Dup Therapy (0)   Dose (0)

1005 — EHR Web App displays returned data for selected patient

*FIG. 6*

Prior Art

Smith, Sam P.
Age: 73 | Sex M | MRN 933145526

| Problems | Immunizations | Meds | Allergies |

Active Problems ▽    Type ▽

| Name | ICD-10 | Managed By |
|---|---|---|
| Problems | | |
| Asthma | J45.909 | Dr. Leonard Spo... |
| Migraine Headache | G43.909 | Dr. William Kirk... |

DUR Alerts:    Drug-Drug (0)    PAR (0)    Disease (...

---

Smith, Sam P.
73y | Male | 933145526

▽ Clinical Information

△ Encounters
△ Medications
△ Diagnoses
△ Allergies
▽ Problems
     Diabetes Mellitus
     Chest Pain
     Migraine
     SNAFU syndrom
     Asthma
△ Labs
△ Pathology
△ Immunizations Community Agent 2016 — Community Agent Application displays returned data for selected patient in overlay interface

FIG. 12

Smith, Sam P.
Age: 73 | Sex M | MRN 9331145526

| Problems | Immunizations | Meds | Allergies | Orders | Patient Worklist | Chart Viewer |

[Type ▽] ☑ Show Community Data    [Commit]

Active Problems ▽

| Name | ICD-10 | Managed By | Last Assessed |
|---|---|---|---|
| Problems | | | |
| Asthma | J45.909 | Dr. Leonard Spock (Cardiac) | 09 Oct 2016 |
| Migraine Headache | G43.909 | Dr. William Kirk (Internal Medicine) | 13 Sep 2016 |
| Diabetes Mellitus | | | |
| Chest Pain | R07.9 | | 01 May 2016 |
| SNAFU syndrom | | | |

DUR Alerts:  Drug-Drug (0)   PAR (0)   Disease (1)   Dup Therapy (0)   Dose (0)

*FIG. 23*

| Problems | Immunizations | Meds | Allergies | Orders | Patient Worklist | Chart Viewer |
|---|---|---|---|---|---|---|

Smith, Sam P.
Age: 73 | Sex M | MRN 9331145526

Active Problems ▽ | Type ▽ | ☑ Show Community Data | Commit

| Name | ICD-10 | Managed By | Last Assessed |
|---|---|---|---|
| Problems | | | |
| Asthma | J45.909 | | |
| Migraine Headache | G43.909 | Dr. Leonard Spock (Cardiac) | 09 Oct 2016 |
| Diabetes Mellitus | | Dr. William Kirk (Internal Medicine) | 13 Sep 2016 |
| Chest Pain | R07.9 | | |
| SNAFU syndrom | | | |
| Potential Duplicates | | | |
| Migraine Headache | G43.909 | | 01 May 2016 |

DUR Alerts:  Drug-Drug (0)   PAR (0)   Disease (1)   Dup Therapy (0)   Dose (0)

*FIG. 25*

Smith, Sam P.
Age: 73 | Sex M | MRN 9331145526

Search

| Problems | Immunizations | Meds | Allergies | Orders | Patient Worklist | Chart Viewer |

Active Problems ▽   Type ▽                    ☑ Show Community Data                Commit

| Name | ICD-10 | Managed By | Last Assessed |
|---|---|---|---|
| Problems | | | |
| Asthma | J45.909 | Dr. Leonard Spock (Cardiac) | 09 Oct 2016 |
| Migraine Headache | G43.909 | Dr. William Kirk (Internal Medicine) | 13 Sep 2016 |
| Diabetes Mellitus | | | 01 May 2016 |

Diabetes Mellitus                                        Close

Select a potential match to import:     Results: (2)

Type to filter list below

E10 Type 1 Diabetes Mellitus
E11 Type 2 Diabetes Mellitus

Don't see a good match? Try searching.

DUR Alerts:  Disease (1)   Dup Therapy (0)   Dose (0)

*FIG. 26*

Problems | Immunizations | Meds | Allergies | Orders | Patient Worklist | Chart Viewer Smith, Sam P.
Age: 73 | Sex M | MRN 9331145526

Active Problems ▽ | Type ▽ | ☑ Show Community Data | Commit

| Name | ICD-10 | Managed By | Last Assessed |
|---|---|---|---|
| Problems | | | |
| Asthma | J45.909 | | |
| Migraine Headache | G43.909 | Dr. Leonard Spock (Cardiac) | 09 Oct 2016 |
| Type 1 Diabetes Mellitus | E10 | Dr. William Kirk (Internal Medicine) | 13 Sep 2016 |
| Chest Pain | R07.9 | | |
| SNAFU syndrom | | | |
| Potential Duplicates | | | |
| Migraine Headache | G43.909 | | 01 May 2016 |

DUR Alerts:  Drug-Drug (0)   PAR (0)   Disease (1)   Dup Therapy (0)   Dose (0)

| Smith, Sam P. | | | | | | |
|---|---|---|---|---|---|---|
| Age: 73 \| Sex M \| MRN 9331145526 | | | | | | |
| Problems | Immunizations | Meds | Allergies | Orders | Patient Worklist | Chart Viewer |

Active Problems ▽ | Type ▽ | ☑ Show Community Data | | Commit

| | Name | ICD-10 | Managed By | Last Assessed |
|---|---|---|---|---|
| | Problems | | | |
| ⊞ | Asthma | J45.909 | | |
| ⊞ | Migraine Headache | G43.909 | Dr. Leonard Spock (Cardiac) | 09 Oct 2016 |
| ⊞ | Type 1 Diabetes Mellitus | E10 | Dr. William Kirk (Internal Medicine) | 13 Sep 2016 |
| | Chest Pain | R07.9 | | |
| | Potential Duplicates | | | |
| ⊞ | Migraine Headache | G43.909 | | 01 May 2016 |

DUR Alerts:   Drug-Drug (0)   PAR (0)   Disease (1)   Dup Therapy (0)   Dose (0)

*FIG. 31*

Smith, Sam P.
Age: 73 | Sex M | MRN 9331145526

| Problems | Immunizations | Meds | Allergies | Orders | Patient Worklist | Chart Viewer |

Active Problems ▽ | Type ▽ | ☑ Show Community Data | Commit

| Name | ICD-10 | Managed By | Last Assessed |
|---|---|---|---|
| Problems | | | |
| Asthma | J45.909 | | |
| Migraine Headache | G43.909 | Dr. Leonard Spock (Cardiac) | 09 Oct 2016 |
| Type 1 Diabetes Mellitus | E10 | Dr. William Kirk (Internal Medicine) | 13 Sep 2016 |
| Chest Pain | R07.9 | | |
| Potential Duplicates | | | |
| Migraine Headache | G43.909 | | 01 May 2016 |

Alergic to: ☑ Acetaminophen

DUR Alerts: Drug-Drug (0) PAR (0) Disease (1) Dup Therapy (0) Dose (0)

*FIG. 32*

METHODS, SYSTEMS AND APPARATUS FOR PROCESSING AND DISPLAYING COMMUNITY PATIENT DATA ALONGSIDE NATIVE PATIENT DATA

COPYRIGHT STATEMENT

All of the material in this patent document, including computer source code if any, is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to graphical user interface methodologies and other methodologies for facilitating display of electronic healthcare record (EHR) data that is received from multiple sources.

In the provision of healthcare, EHR systems are becoming increasingly ubiquitous. There exists a large number of different EHR systems offered by various vendors, and these EHR systems can utilize a wide variety of different system architectures and data schemas. For example, these EHR systems can comprise traditional applications, web applications, thin-client applications, and cloud applications, and could be distributed over one or more local area networks, wide area networks, the Internet, and combinations thereof.

These EHR systems typically allow a provider to easily access electronic healthcare records for patients which are stored in a data store. Generally, each EHR systems is configured for use with one or more particular data stores of a healthcare system in which electronic healthcare records are formatted in a way particular to such healthcare or EHR system.

FIG. 1 illustrates an exemplary methodology in an exemplary EHR system by which an EHR application in the form of an EHR web application that is loaded in a web browser accesses EHR data for a particular patient from a database in the EHR system. The methodology begins at step 1001 when a user selects a patient in an interface of the EHR web application, as illustrated in FIG. 2. This represents a new patient context. In response to this, at step 1002, the EHR web app requests data for that patient from an EHR web service at an EHR web server in the EHR system, as illustrated in FIG. 3. Next, at step 1003, the EHR web service accesses data for that patient from an EHR database or data store at an EHR DB server of the EHR system, as illustrated in FIG. 4. At step 1004, the EHR web service returns data for that patient to the EHR web app, as illustrated in FIG. 5. At step 1005, the EHR web app processes the received data for that patient and displays patient information for that patient as illustrated in FIG. 6.

It will be appreciated that this process results in display of information for that patient which is stored in the EHR database in the particular EHR system, but that there might be other information for that patient available elsewhere in databases of other EHR systems. Many have recognized this shortcoming and have attempted to develop solutions to address or alleviate it. For example, one solution which has been developed involves aggregating data from a plurality of EHR systems at a community data store, and utilizing a supplemental community agent application which displays additional data for a patient in an overlay interface. FIGS. 7 and 8 serve to illustrate an exemplary methodology and system that incorporates such a supplemental community agent application.

First, as will be appreciated from a comparison of FIGS. 3 and 8, the same web browser, EHR web app, EHR web service, EHR web server, EHR database, and EHR DB server are used. Second, the methodology illustrated in FIG. 7 includes steps 2001,2002,2003,2004,2005 that compare to the steps of the methodology of FIG. 1, which serve to retrieve patient data from the EHR database. Additionally, when a user selects a patient in the EHR web app, the community agent application intercepts (or receives) patient context information from the EHR web app. This occurs at step 2012, and represents the kickoff point for a separate flow for retrieving data for that patient from a community server for display in an overlay interface of the community agent application.

In this regard, at step 2013 the community agent application requests community data from a community service running on a community server, as illustrated in FIG. 9. At step 2014, the community service accesses community data for the patient from a community data store or database, which may be co-located with the community service. Alternatively, the community service accesses the community data from a community database at a community DB server, as illustrated for example in FIG. 10. In either case, at step 2015 the community service returns community data for the patient to the community agent application, as illustrated in FIG. 11. At step 2016, the community agent application displays returned data for the patient in an overlay interface, as illustrated in FIG. 12.

The overlay interface succeeds in providing supplemental information from sources other than the EHR database associated with the EHR web app to a user of the EHR web app, but requires installing and running two separate software applications, and further requires that the user interact with both the EHR web app and the overlay interface of the community agent application in order to view all of the available information. Sometimes, the user will spend time navigating the overlay interface of the community agent application only to discover that all of the data in the community agent application is duplicative of information in the EHR web app. Sometimes, with more complex data sets, the user will even struggle to identify what is duplicative or distinct. Additionally, such a community agent application may use different vocabulary and formatting conventions from the EHR web app, leading to inefficiencies in comprehending, assimilating, and navigating the information.

In view of the foregoing, one or more needs are believed to exist for improvements in facilitating access, display, and use of EHR data of a patient from multiple sources. This, and other needs, are believed to be addressed by one or more aspects and features of the invention.

SUMMARY OF THE INVENTION

The present invention includes many aspects and features.
A first aspect of the present invention relates to a method for facilitating integration of patient electronic healthcare record information from a community aggregator with electronic healthcare record information native to an electronic healthcare record (EHR) application comprises: (a) receiving, via a first interface of an EHR web app loaded in a web browser running on a user device, first user input corresponding to selection of a patient effecting a new patient context; (b) in response thereto, (i) effecting a first asynchronous flow involving (A) communicating, from the EHR web app to an EHR web service at an EHR web server, a request for native patient data for the patient, (B) accessing, by the EHR web service, native patient data for the patient, (C) returning, from the EHR web service to the EHR web app, the accessed native patient data, and (ii) effecting a second asynchronous flow involving (A) communicating, from the EHR web app to an EHR community service at the EHR web server, a request for community patient data for the patient, (B) communicating, from the EHR community service to a community service at a community server, a request for community patient data for the patient, (C) accessing, by the community service, community patient data for the patient, (D) returning, from the community service to the EHR community service, the accessed community patient data, (E) returning, from the EHR community service to the EHR web app, the accessed community patient data, (iii) in response to completion of the first asynchronous flow and the second asynchronous flow, processing the accessed community patient data by (A) for each community data item of a plurality of community data items in the accessed community patient data, (1) comparing the community data item to native data items in the accessed native patient data in order, and (2) based on the comparison, identifying the community data item as (I) a duplicate, (II) a potential duplicate, or (III) not a duplicate, and (B) for each community data item of the plurality of community data items which was not identified as a duplicate, (1) comparing the community data item to entries in one or more native clinical dictionaries, and (2) based on the comparison, identifying the community data item as (I) an exact match to a clinical dictionary entry, (II) a potential match to one or more clinical dictionary entries, or (III) not matched to any clinical dictionary entry, and (iv) displaying, in a second interface of the EHR web app, (A) a listing for each of (1) one or more native data items from the accessed native patient, (2) one or more community data items that were identified to be a definite match to a clinical dictionary entry, (3) one or more community data items that were identified to be a potential match to one or more clinical dictionary entries, (4) one or more community data items that were identified as not being matched to any clinical dictionary entry, and (5) one or more community data items that were identified as a potential duplicate, (6) wherein there is no listing displayed for any community data item identified as a duplicate, (B) for each listing for one of the community data items that was identified to be a definite match to a clinical dictionary entry, a visual indication that the listing is for a community data item that was identified to be a definite match, (C) for each listing for one of the community data items that was identified to be a potential match to a clinical dictionary entry, a visual indication that the listing is for a community data item that was identified to be a potential match, (D) for each listing for one of the community data items that was identified as not being matched to any clinical dictionary entry, a visual indication that the listing is for a community data item that was identified that was identified as not being matched to any clinical dictionary entry, (E) one or more visual indications that the one or more community data items that were identified as a potential duplicate are potential duplicates, (c) receiving, via the second interface of the EHR web app, second user input corresponding to interaction with the listing for a first community data item, the first community data item being one of the community data items that was identified to be a definite match to a clinical dictionary entry, and the interaction representing an indication to import the first community data item in the EHR web app; (d) automatically converting, in response to the second user input, the first community data item to a native data item based on the clinical dictionary entry it was identified to be a definite match to; (e) receiving, via the second interface of the EHR web app, third user input corresponding to interaction with the listing for a second community data item, the second community data item being one of the community data items that was identified to be a potential match to one or more clinical dictionary entries, and the interaction representing an indication to import the second community data item in the EHR web app; (f) displaying, in response to the third user input, a third interface of the EHR web app which includes a listing for each of the clinical dictionary entries that the second community data item was identified to be a potential match to; (g) receiving, via the third interface of the EHR web app, fourth user input corresponding to selection of one of the listed clinical dictionary entries; and (h) automatically converting, based on the fourth user input, the second community data item to a native data item based on the selected clinical dictionary entry.

In a feature, communicating, from the EHR community service to a community service at a community server, a request for community patient data for the patient comprises making an API call.

In a feature, communicating, from the EHR community service to a community service at a community server, a request for community patient data for the patient comprises accessing a URL.

In a feature, communicating, from the EHR community service to a community service at a community server, a request for community patient data for the patient comprises communicating a request including a parameter specifying one or more filter options.

In a feature, returning, from the community service to the EHR community service, the accessed community patient data comprises returning a virtual patient object.

In a feature, the method further comprises receiving, from the user, user input corresponding to an indication to suppress one or the displayed community data items. The method may further comprise updating an interface of the EHR web app to no longer display the suppressed community data item; and storing, in a suppression data table, a source identifier and a source item identifier for the community item to be suppressed, and subsequently comparing loaded community items to information stored in the suppression data table to determine whether to suppress the loaded community items.

In a feature, the user device comprises a laptop.
In a feature, the user device comprises a desktop computer.
In a feature, the user device comprises a tablet.
In a feature, the user device comprises a slate computer.
In a feature, the user device comprises a phone.
In a feature, the user device comprises a smart appliance.

In another aspect, a method for facilitating integration of patient electronic healthcare record information from a community aggregator with electronic healthcare record information native to an electronic healthcare record (EHR) application comprises: (a) receiving, via a first interface of an EHR web app loaded in a web browser running on a user device, first user input corresponding to selection of a patient effecting a new patient context; (b) in response thereto, (i) effecting a first asynchronous flow involving (A) communicating, from the EHR web app to an EHR web service at an EHR web server, a request for native patient data for the patient, (B) accessing, by the EHR web service, native patient data for the patient, (ii) effecting a second asynchronous flow involving (A) communicating, from the EHR web app to an EHR community service at the EHR web server, a request for community patient data for the patient, (B) communicating, from the EHR community service to a community service at a community server, a request for community patient data for the patient, (C) accessing, by the community service, community patient data for the patient, (D) returning, from the community service to the EHR community service, the accessed community patient data, (iii) in response to completion of the first asynchronous flow and the second asynchronous flow, processing the accessed community patient data at the EHR web server by (A) for each community data item of a plurality of community data items in the accessed community patient data, (1) comparing the community data item to native data items in the accessed native patient data in order, and (2) based on the comparison, identifying the community data item as (I) a duplicate, (II) a potential duplicate, or (III) not a duplicate, and (B) for each community data item of the plurality of community data items which was not identified as a duplicate, (1) comparing the community data item to entries in one or more native clinical dictionaries, and (2) based on the comparison, identifying the community data item as (I) an exact match to a clinical dictionary entry, (II) a potential match to one or more clinical dictionary entries, or (III) not matched to any clinical dictionary entry, and (iv) displaying, in a second interface of the EHR web app, (A) a listing for each of (1) one or more native data items from the accessed native patient data, (2) one or more community data items that were identified to be a definite match to a clinical dictionary entry, (3) one or more community data items that were identified to be a potential match to one or more clinical dictionary entries, (4) one or more community data items that were identified as not being matched to any clinical dictionary entry, and (5) one or more community data items that were identified as a potential duplicate, (6) wherein there is no listing displayed for any community data item identified as a duplicate, (B) for each listing for one of the community data items that was identified to be a definite match to a clinical dictionary entry, a visual indication that the listing is for a community data item that was identified to be a definite match, (C) for each listing for one of the community data items that was identified to be a potential match to a clinical dictionary entry, a visual indication that the listing is for a community data item that was identified to be a potential match, (D) for each listing for one of the community data items that was identified as not being matched to any clinical dictionary entry, a visual indication that the listing is for a community data item that was identified that was identified as not being matched to any clinical dictionary entry, (E) one or more visual indications that the one or more community data items that were identified as a potential duplicate are potential duplicates, (c) receiving, via the second interface of the EHR web app, second user input corresponding to interaction with the listing for a first community data item, the first community data item being one of the community data items that was identified to be a definite match to a clinical dictionary entry, and the interaction representing an indication to import the first community data item in the EHR web app; (d) automatically converting, in response to the second user input, the first community data item to a native data item based on the clinical dictionary entry it was identified to be a definite match to; (e) receiving, via the second interface of the EHR web app, third user input corresponding to interaction with the listing for a second community data item, the second community data item being one of the community data items that was identified to be a potential match to one or more clinical dictionary entries, and the interaction representing an indication to import the second community data item in the EHR web app; (f) displaying, in response to the third user input, a third interface of the EHR web app which includes a listing for each of the clinical dictionary entries that the second community data item was identified to be a potential match to; (g) receiving, via the third interface of the EHR web app, fourth user input corresponding to selection of one of the listed clinical dictionary entries; and (h) automatically converting, based on the fourth user input, the second community data item to a native data item based on the selected clinical dictionary entry.

In another aspect, a method for facilitating integration of patient electronic healthcare record information from a community aggregator with electronic healthcare record information native to an electronic healthcare record (EHR) system, comprises: (a) receiving, via a first interface of an EHR application of the EHR system running on a user device, first user input corresponding to selection of a patient effecting a new patient context; (b) in response thereto, (i) effecting a first asynchronous flow involving (A) communicating, from the EHR application to an EHR web service at an EHR web server, a request for native patient data for the patient, (B) accessing, by the EHR web service, native patient data for the patient, and (C) returning, from the EHR web service to the EHR application, the accessed native patient data, and (ii) effecting a second asynchronous flow involving (A) communicating, from the EHR application to an EHR community service at the EHR web server, a request for community patient data for the patient, (B) communicating, from the EHR community service to a community service at a community server, a request for community patient data for the patient, (C) accessing, by the community service, community patient data for the patient, (D) returning, from the community service to the EHR community service, the accessed community patient data, and (E) returning, from the EHR community service to the EHR application, the accessed community patient data, (iii) in response to completion of the first asynchronous flow and the second asynchronous flow, processing the accessed community patient data by (A) for each community data item of a plurality of community data items in the accessed community patient data, (1) comparing the community data item to native data items in the accessed native patient data in order, and (2) based on the comparison, identifying the community data item as (I) a duplicate, (II) a potential duplicate, or (III) not a duplicate, and (B) for each community data item of the plurality of community data items which was not identified as a duplicate, (1) comparing the community data item to entries in one or more native clinical dictionaries, and (2) based on the comparison, identifying the community data item as (I) an exact match to a clinical dictionary entry, (II) a potential match to one or more clinical dictionary entries, or (III) not matched to any clinical dictionary entry, and (iv) displaying, in a second interface of the EHR application, (A) a listing for each of (1) one or more native data items from the accessed native patient, (2) one or more community data items that were identified to be a definite match to a clinical dictionary entry, (3) one or more community data items that were identified to be a potential match to one or more clinical dictionary entries, (4) one or more community data items that were identified as not being matched to any clinical dictionary entry, and (5) one or more community data items that were identified as a potential duplicate, (6) wherein there is no listing displayed for any community data item identified as a duplicate, (B) for each listing for one of the community data items that was identified to be a definite match to a clinical dictionary entry, a visual indication that the listing is for a community data item that was identified to be a definite match, (C) for each listing for one of the community data items that was identified to be a potential match to a clinical dictionary entry, a visual indication that the listing is for a community data item that was identified to be a potential match, (D) for each listing for one of the community data items that was identified as not being matched to any clinical dictionary entry, a visual indication that the listing is for a community data item that was identified that was identified as not being matched to any clinical dictionary entry, and (E) one or more visual indications that the one or more community data items that were identified as a potential duplicate are potential duplicates, (c) receiving, via the second interface of the EHR application, second user input corresponding to interaction with the listing for a first community data item, the first community data item being one of the community data items that was identified to be a definite match to a clinical dictionary entry, and the interaction representing an indication to import the first community data item in the EHR application; (d) automatically converting, in response to the second user input, the first community data item to a native data item based on the clinical dictionary entry it was identified to be a definite match to; (e) receiving, via the second interface of the EHR application, third user input corresponding to interaction with the listing for a second community data item, the second community data item being one of the community data items that was identified to be a potential match to one or more clinical dictionary entries, and the interaction representing an indication to import the second community data item in the EHR application; (f) displaying, in response to the third user input, a third interface of the EHR application which includes a listing for each of the clinical dictionary entries that the second community data item was identified to be a potential match to; (g) receiving, via the third interface of the EHR application, fourth user input corresponding to selection of one of the listed clinical dictionary entries; and (h) automatically converting, based on the fourth user input, the second community data item to a native data item based on the selected clinical dictionary entry.

In a feature, the EHR application comprises a web app.

In a feature, the EHR application comprises a cloud app.

In a feature, the EHR application comprises a desktop application.

In a feature, the EHR application comprises a thin-client application.

Another aspect relates to a method for facilitating integration of patient electronic healthcare record information from a community aggregator with electronic healthcare record information native to an electronic healthcare record (EHR) system. The method includes (a) receiving, via a first interface of an EHR application running on a user device in the EHR system, first user input corresponding to selection of a patient effecting a new patient context; (b) in response thereto, (i) effecting a first asynchronous flow involving (A) communicating, from the EHR application to an EHR web service at an EHR web server, a request for native patient data for the patient, and (B) accessing, by the EHR web service, native patient data for the patient, (ii) effecting a second asynchronous flow involving (A) communicating, from the EHR application to an EHR community service at the EHR web server, a request for community patient data for the patient, (B) communicating, from the EHR community service to a community service at a community server, a request for community patient data for the patient, (C) accessing, by the community service, community patient data for the patient, and (D) returning, from the community service to the EHR community service, the accessed community patient data, (iii) in response to completion of the first asynchronous flow and the second asynchronous flow, processing the accessed community patient data at the EHR web server by (A) for each community data item of a plurality of community data items in the accessed community patient data, (1) comparing the community data item to native data items in the accessed native patient data in order, and (2) based on the comparison, identifying the community data item as (I) a duplicate, (II) a potential duplicate, or (III) not a duplicate, and (B) for each community data item of the plurality of community data items which was not identified as a duplicate, (1) comparing the community data item to entries in one or more native clinical dictionaries, and (2) based on the comparison, identifying the community data item as (I) an exact match to a clinical dictionary entry, (II) a potential match to one or more clinical dictionary entries, or (III) not matched to any clinical dictionary entry, and (iv) displaying, in a second interface of the EHR application, (A) a listing for each of (1) one or more native data items from the accessed native patient data, (2) one or more community data items that were identified to be a definite match to a clinical dictionary entry, (3) one or more community data items that were identified to be a potential match to one or more clinical dictionary entries, (4) one or more community data items that were identified as not being matched to any clinical dictionary entry, and (5) one or more community data items that were identified as a potential duplicate, (6) wherein there is no listing displayed for any community data item identified as a duplicate, (B) for each listing for one of the community data items that was identified to be a definite match to a clinical dictionary entry, a visual indication that the listing is for a community data item that was identified to be a definite match, (C) for each listing for one of the community data items that was identified to be a potential match to a clinical dictionary entry, a visual indication that the listing is for a community data item that was identified to be a potential match, (D) for each listing for one of the community data items that was identified as not being matched to any clinical dictionary entry, a visual indication that the listing is for a community data item that was identified that was identified as not being matched to any clinical dictionary entry, and (E) one or more visual indications that the one or more community data items that were identified as a potential duplicate are potential duplicates, (c) receiving, via the second interface of the EHR application, second user input corresponding to interaction with the listing for a first community data item, the first community data item being one of the community data items that was identified to be a definite match to a clinical dictionary entry, and the interaction representing an indication to import the first community data item into the EHR application; (d) automatically converting, in response to the second user input, the first community data item to a native data item based on the clinical dictionary entry it was identified to be a definite match to; (e) receiving, via the second interface of the EHR application, third user input corresponding to interaction with the listing for a second community data item, the second community data item being one of the community data items that was identified to be a potential match to one or more clinical dictionary entries, and the interaction representing an indication to import the second community data item in the EHR application; (f) displaying, in response to the third user input, a third interface of the EHR application which includes a listing for each of the clinical dictionary entries that the second community data item was identified to be a potential match to; (g) receiving, via the third interface of the EHR application, fourth user input corresponding to selection of one of the listed clinical dictionary entries; and (h) automatically converting, based on the fourth user input, the second community data item to a native data item based on the selected clinical dictionary entry.

Another aspect relates to one or more computer readable media for performing a disclosed method.

Another aspect relates to a system for performing a disclosed method.

In addition to the aforementioned aspects and features of the present invention, it should be noted that the present invention further encompasses the various logical combinations and subcombinations of such aspects and features. Thus, for example, claims in this or a divisional or continuing patent application or applications may be separately directed to any aspect, feature, or embodiment disclosed herein, or combination thereof, without requiring any other aspect, feature, or embodiment.

BRIEF DESCRIPTION OF THE DRAWINGS

One or more preferred embodiments of the present invention now will be described in detail with reference to the accompanying drawings, wherein the same elements are referred to with the same reference numerals, and wherein:

FIGS. 1-6 illustrate an exemplary methodology in an exemplary EHR system by which an EHR application in the form of an EHR web application that is loaded in a web browser accesses EHR data for a particular patient from a database in the EHR system;

FIGS. 7-12 illustrate an exemplary methodology and system that incorporates a supplemental community agent application;

FIGS. 23-32 illustrate exemplary functionality in accordance with one or more preferred implementations.

DETAILED DESCRIPTION

Figure 1:
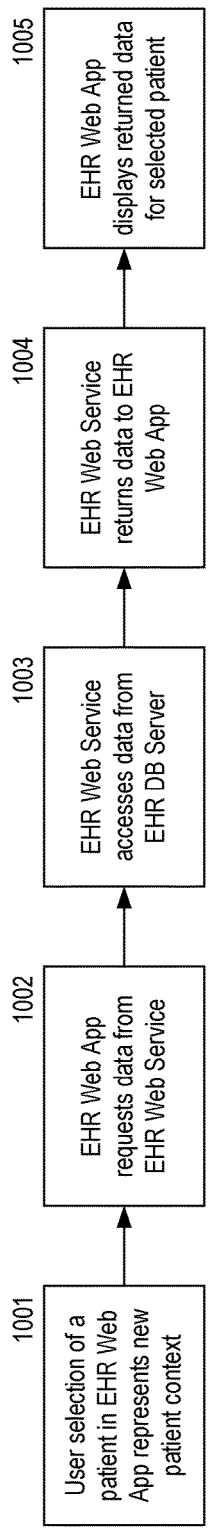
Figure 3:
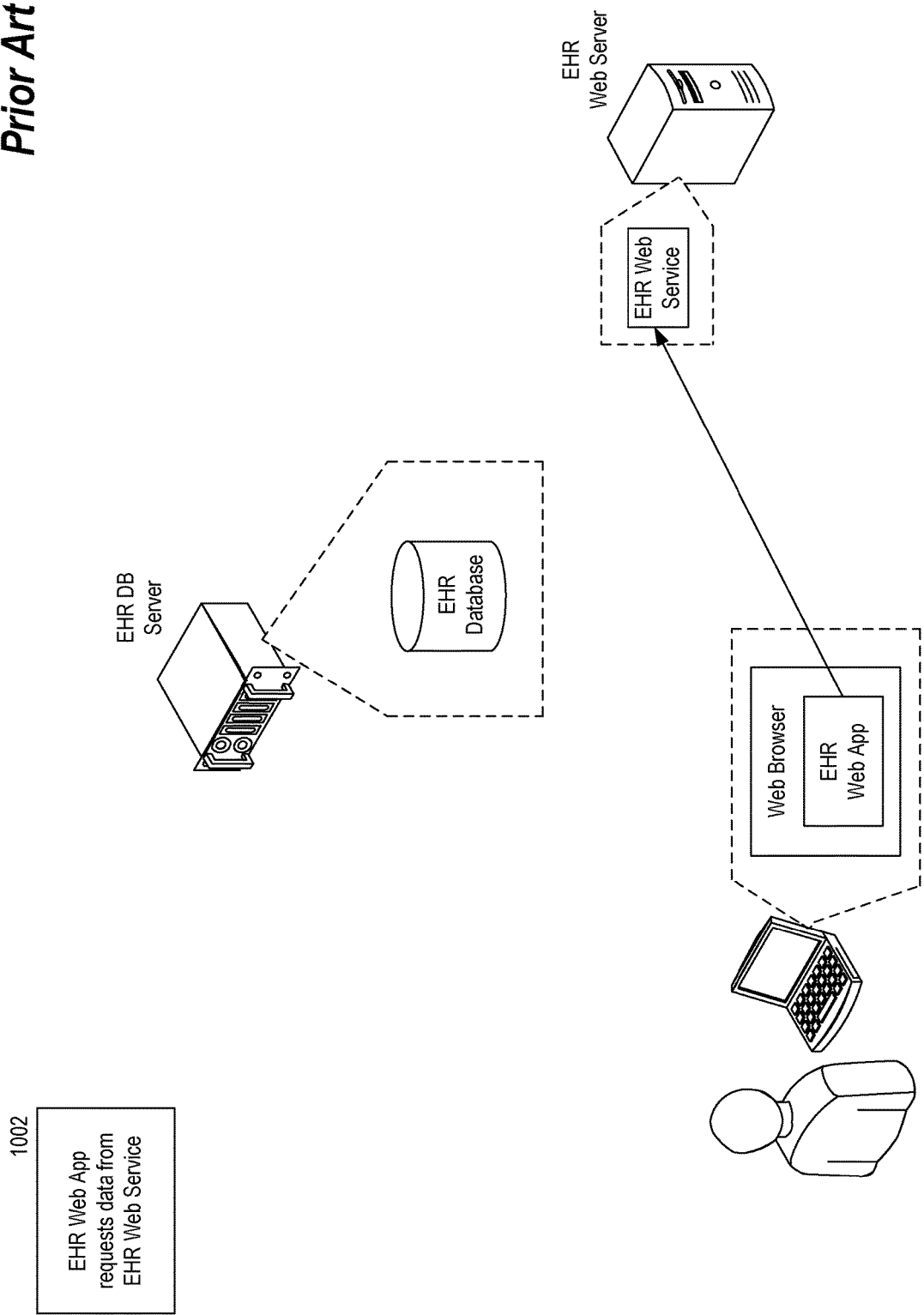
Figure 4:
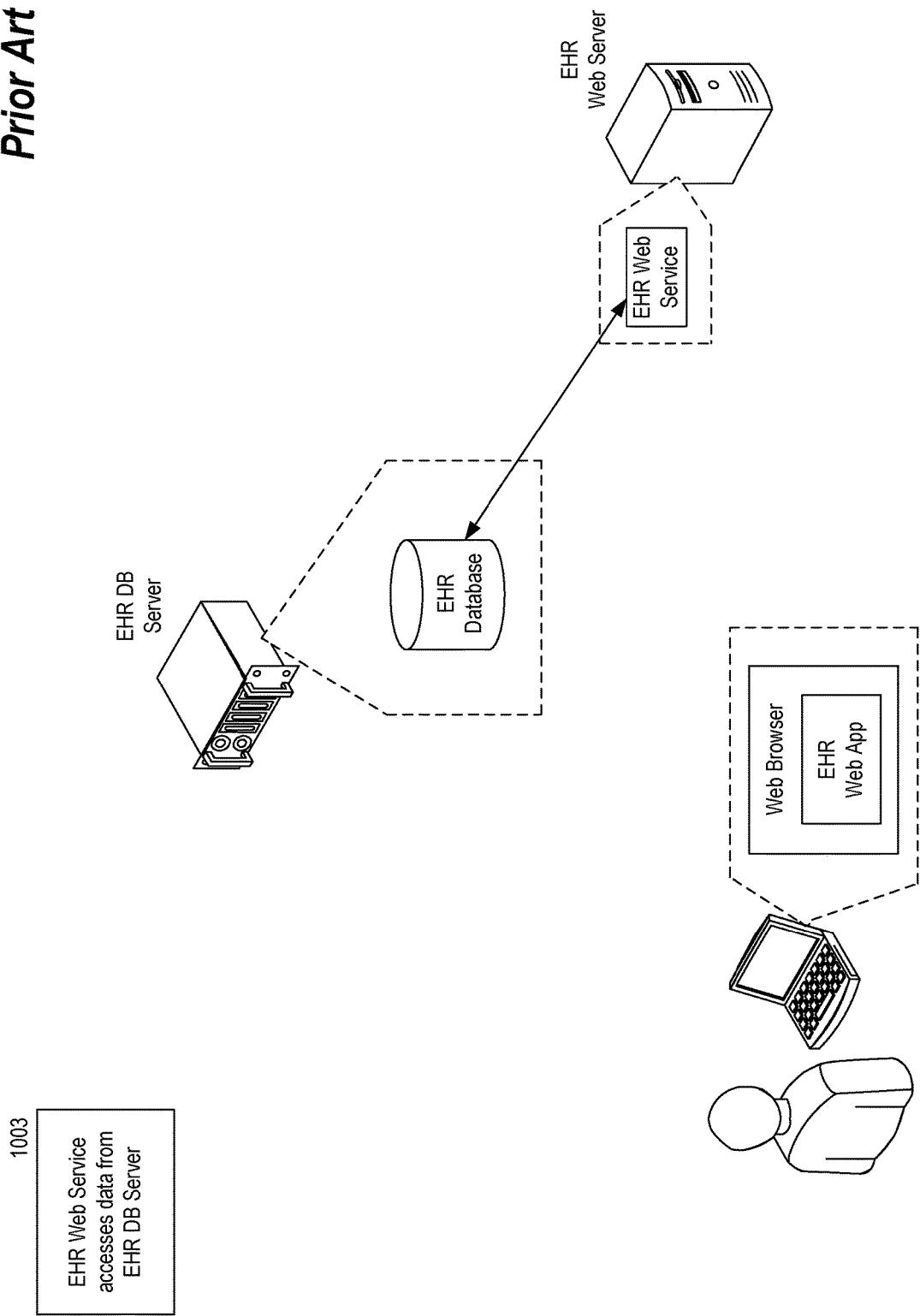
Figure 5:
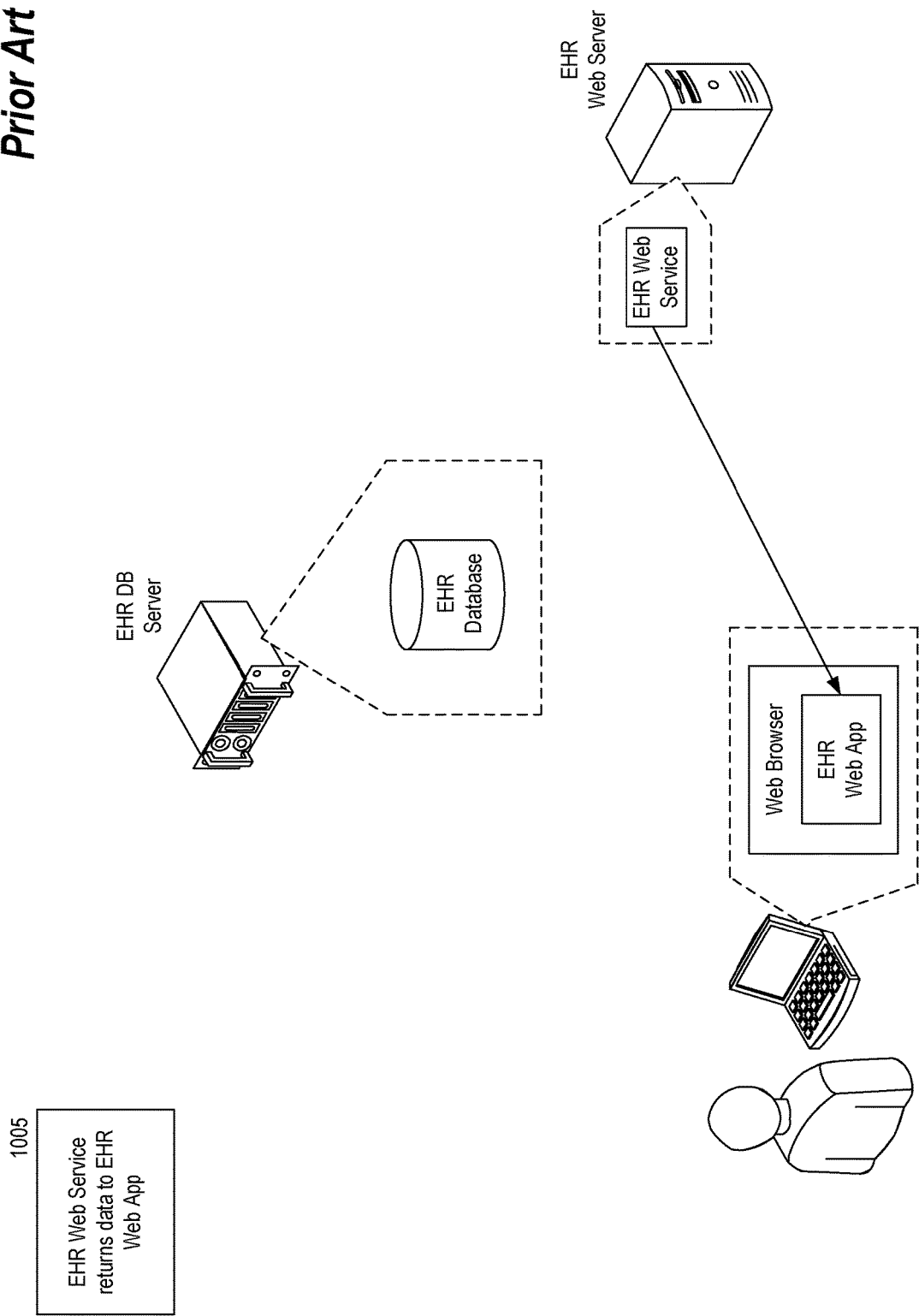
Figure 7:
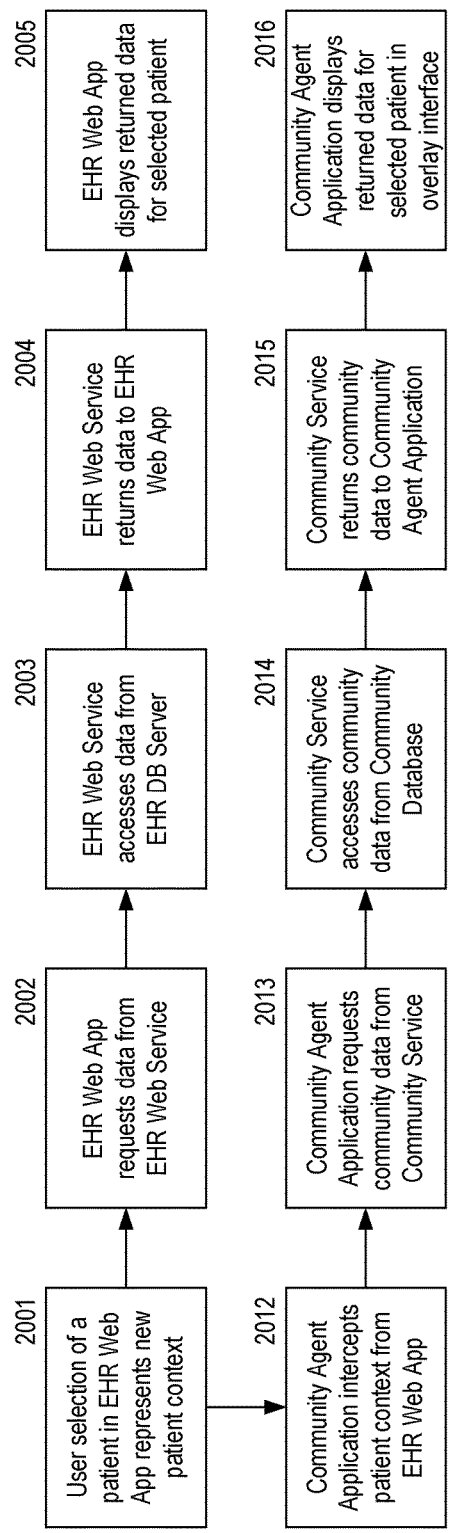
Figure 8:
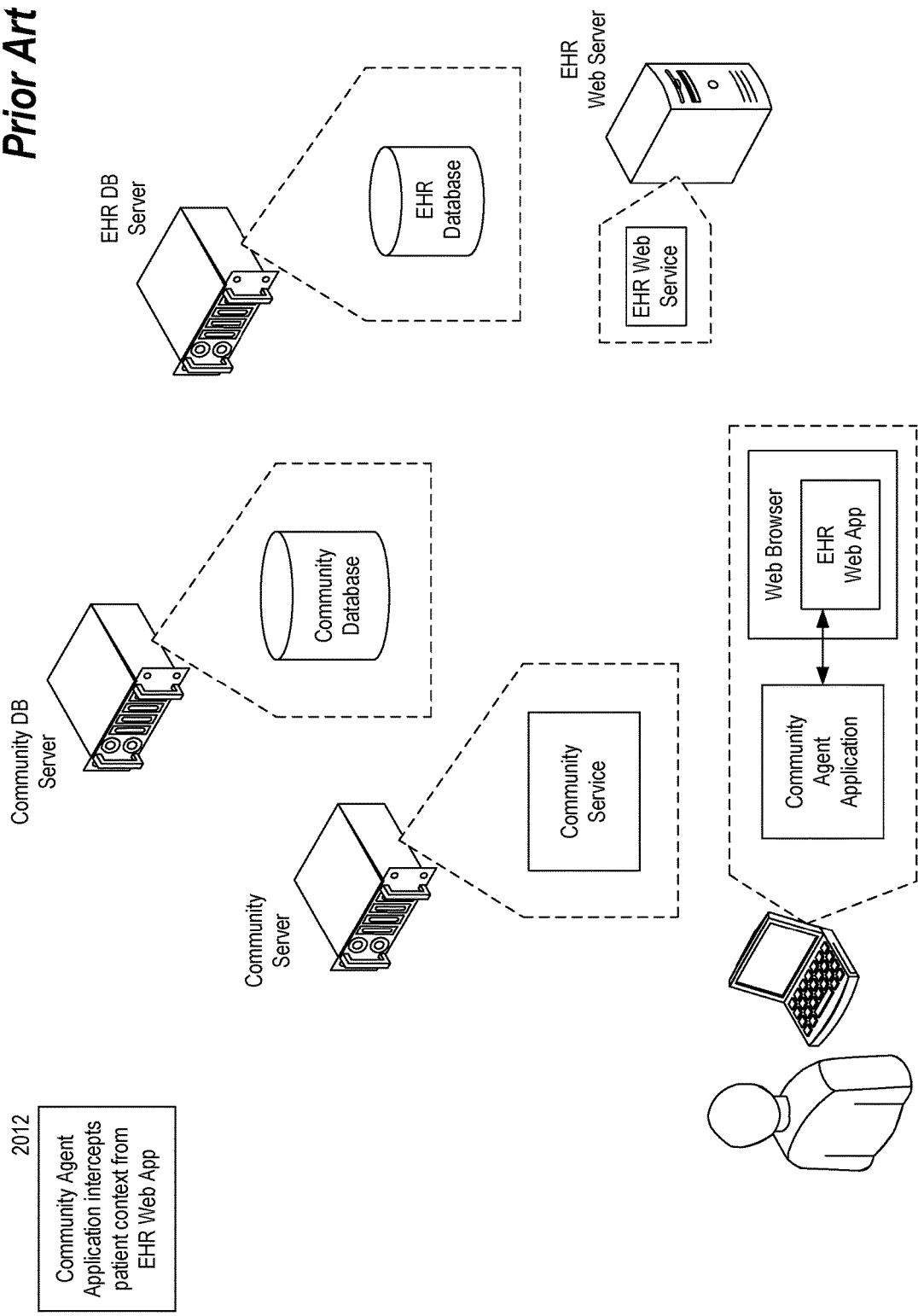
Figure 9:
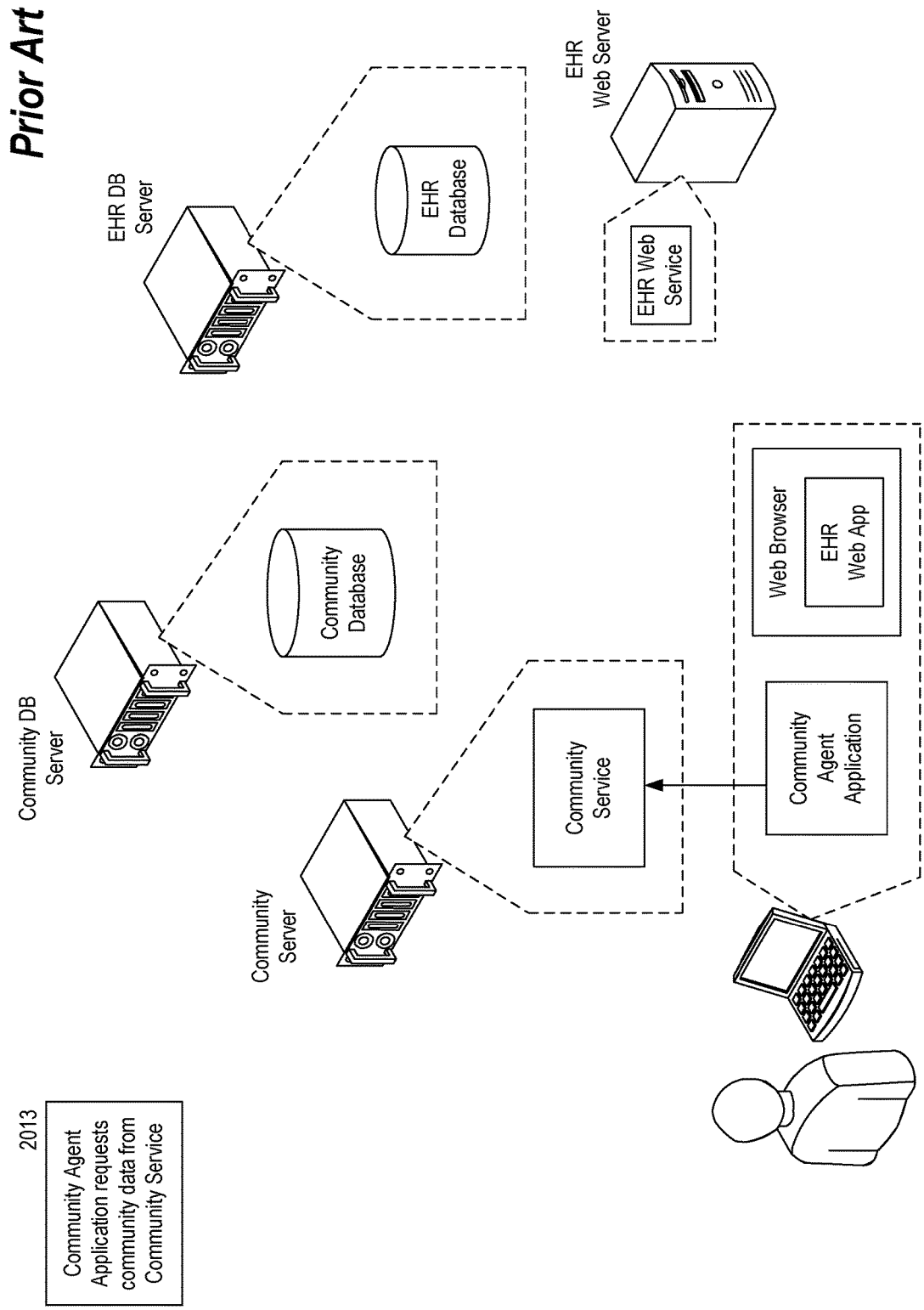

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention, and is made merely for the purposes of providing a full and enabling disclosure of the invention. The detailed disclosure herein of one or more embodiments is not intended, nor is to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

With regard solely to construction of any claim with respect to the United States, no claim element is to be interpreted under 35 U.S.C. 112(f) unless the explicit phrase "means for" or "step for" is actually used in such claim element, whereupon this statutory provision is intended to and should apply in the interpretation of such claim element. With regard to any method claim including a condition precedent step, such method requires the condition precedent to be met and the step to be performed at least once during performance of the claimed method.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." When used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the invention are next described. The following description of one or more preferred embodiments is merely exemplary in nature and is in no way intended to limit the invention, its implementations, or uses.

There has been described hereinabove an EHR system including an EHR application in the specific form of an EHR web app, and a first methodology for directly accessing native EHR data from an EHR database of the EHR system and displaying the accessed native EHR data in the EHR web app. There further has been described within this context a second methodology for receiving EHR data from a community database and displaying that data in conjunction with the EHR web app in an overlay interface using a community agent application.

In contrast, in accordance with one or more preferred implementations of the invention, an EHR application in the form of an EHR web app is configured to receive both native EHR data from one or more data stores associated with the EHR application, and community EHR data from one or more community data stores, and selectively combine and collectively display such information in an interface of the EHR application itself in a manner that promotes efficiency in comprehending, assimilating, and navigating such information. Of course, it will be appreciated that such EHR application need not be a web app per se, and could be in the form of a standalone windows application or other program, including for example, and not by way of limitation, a thin-client application or a cloud application.

Figure 13:
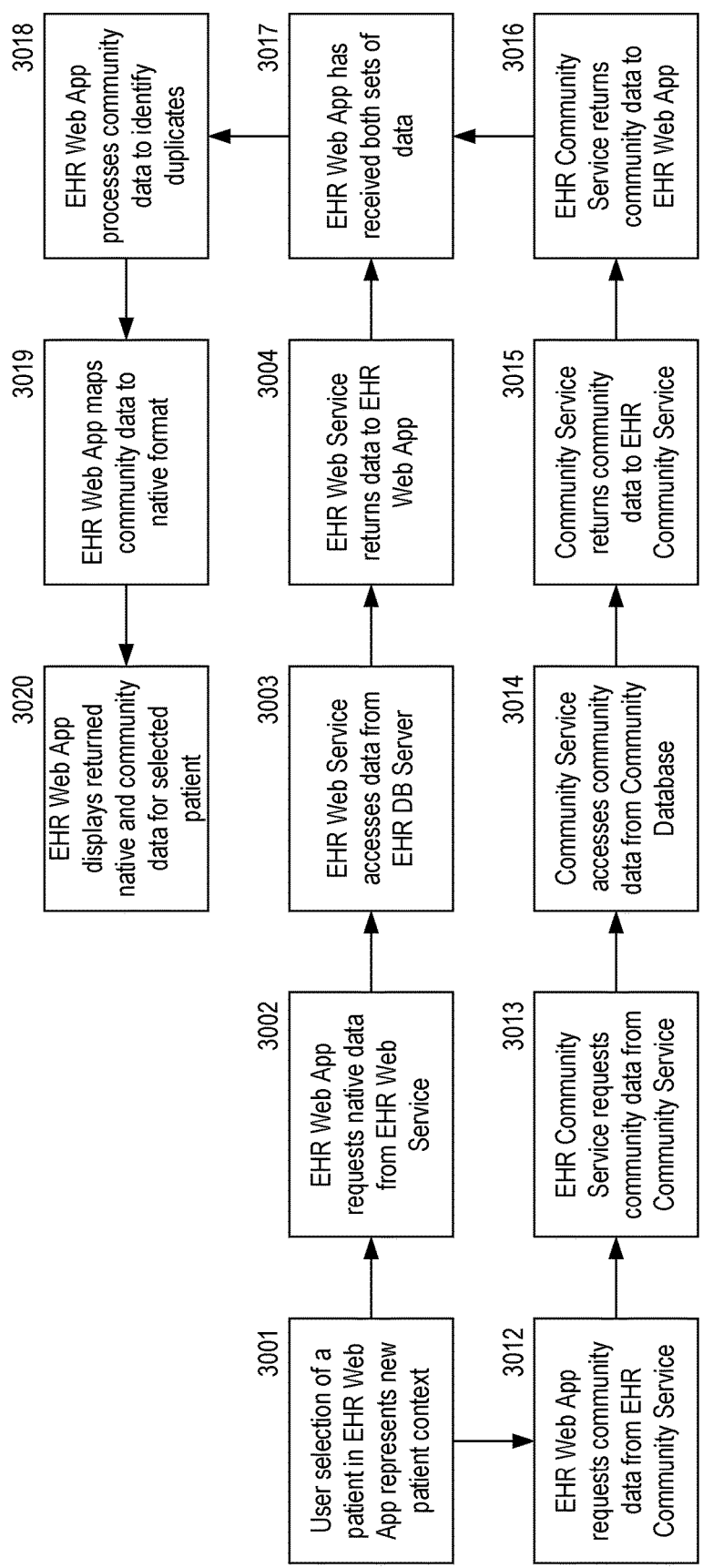
FIGS. 13-22 illustrate an exemplary methodology in accordance with one or more preferred implementations.

Accordingly, FIG. 13 illustrates an exemplary methodology utilized in one or more preferred implementations. The methodology starts with a user selecting a patient in the EHR web app, here at step 3001. The methodology includes steps 3002,3003,3004 which serve to retrieve patient data from the EHR database in the same manner as discussed hereinabove with respect to FIG. 1.

Figure 14:
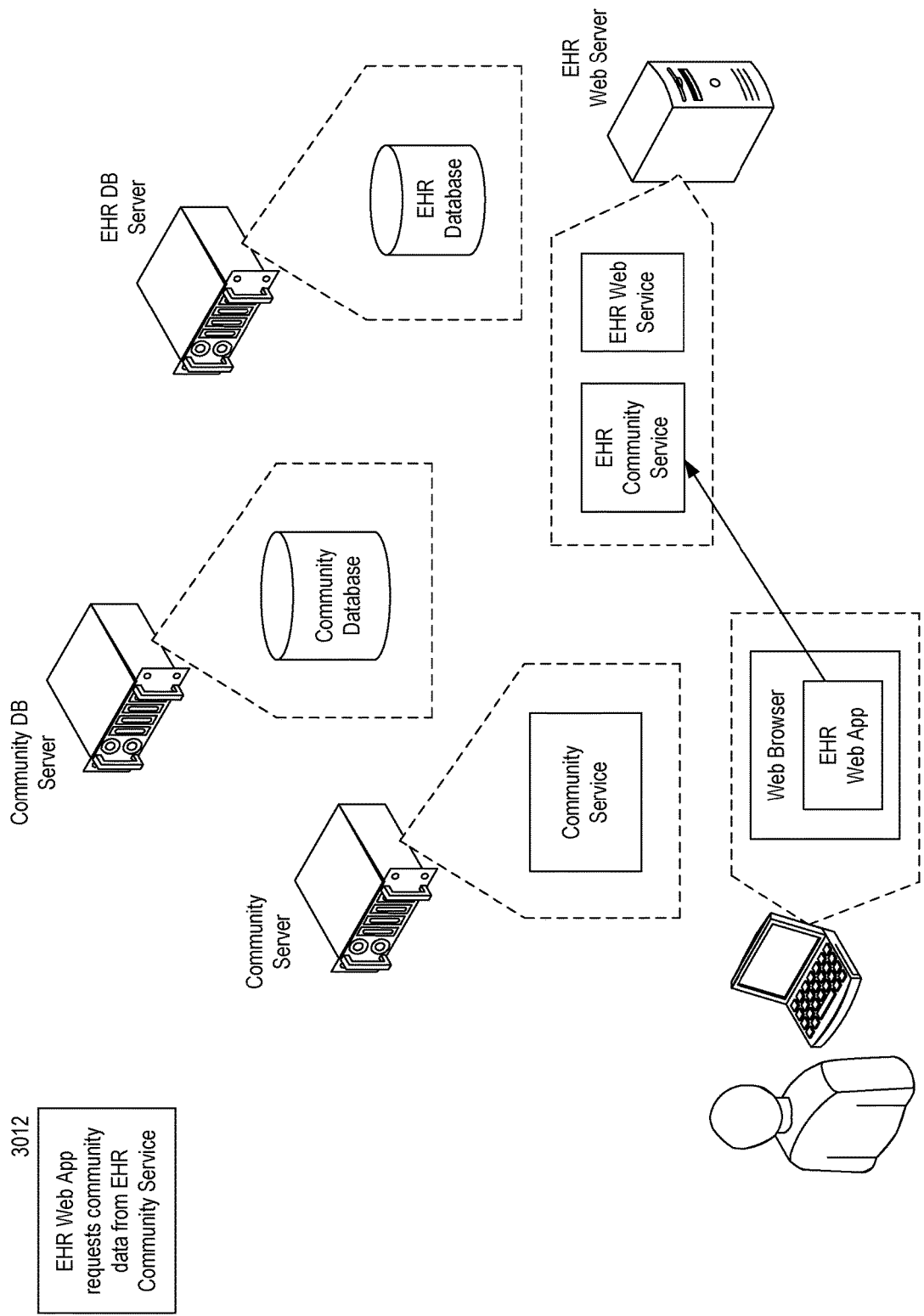
Figure 15:
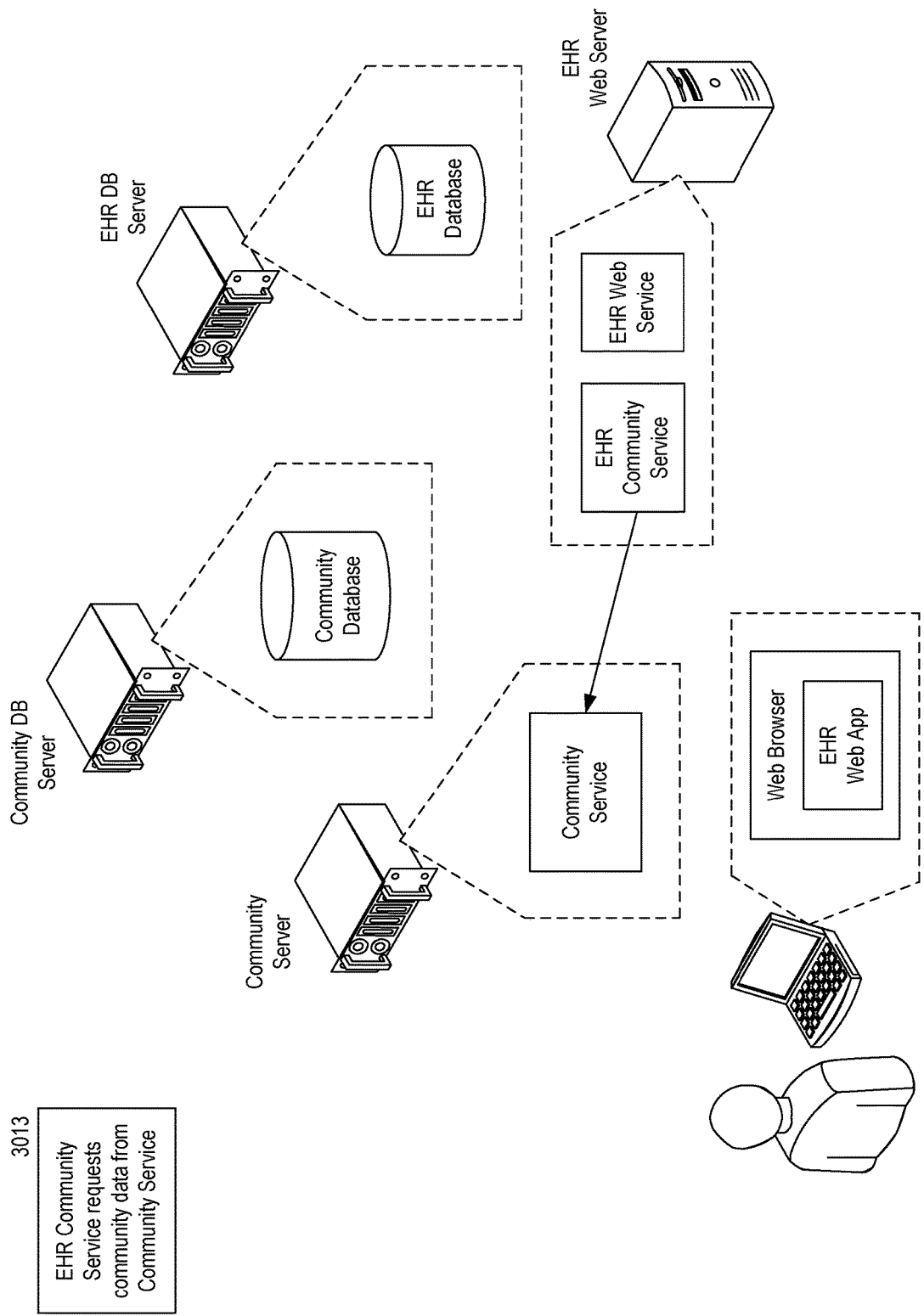

Additionally, however, when a user selects a patient in the EHR web app, a separate asynchronous flow is kicked off by the EHR web app for retrieving data from a community server. This flow starts at step 3012, where the EHR web app requests community data for the patient from an EHR community service at an EHR web server, as illustrated in FIG. 14. At step 3013, the EHR community service in turn requests community data for the patient from a community service loaded on a community server, as illustrated in FIG. 15. This may involve making a call to a service or Application Programming Interface (API), requesting a virtual patient object (VPO) containing medical data for the patient in one or more particular domains (such as problems, allergies medications, or immunizations), or may involve requesting all available medical data for the patient (e.g. in all available domains). For example, a call may be made utilizing a particular uniform resource locator (URL) to request and receive back a returned VPO. In accordance with one or more preferred implementations, a call may include an indication (e.g. in a parameter) of whether the community service should perform one or more filtering operations, including semantic duplicate checking, or whether the community service should return community data without filtering out any items that are determined by the community service to be duplicative.

Figure 10:
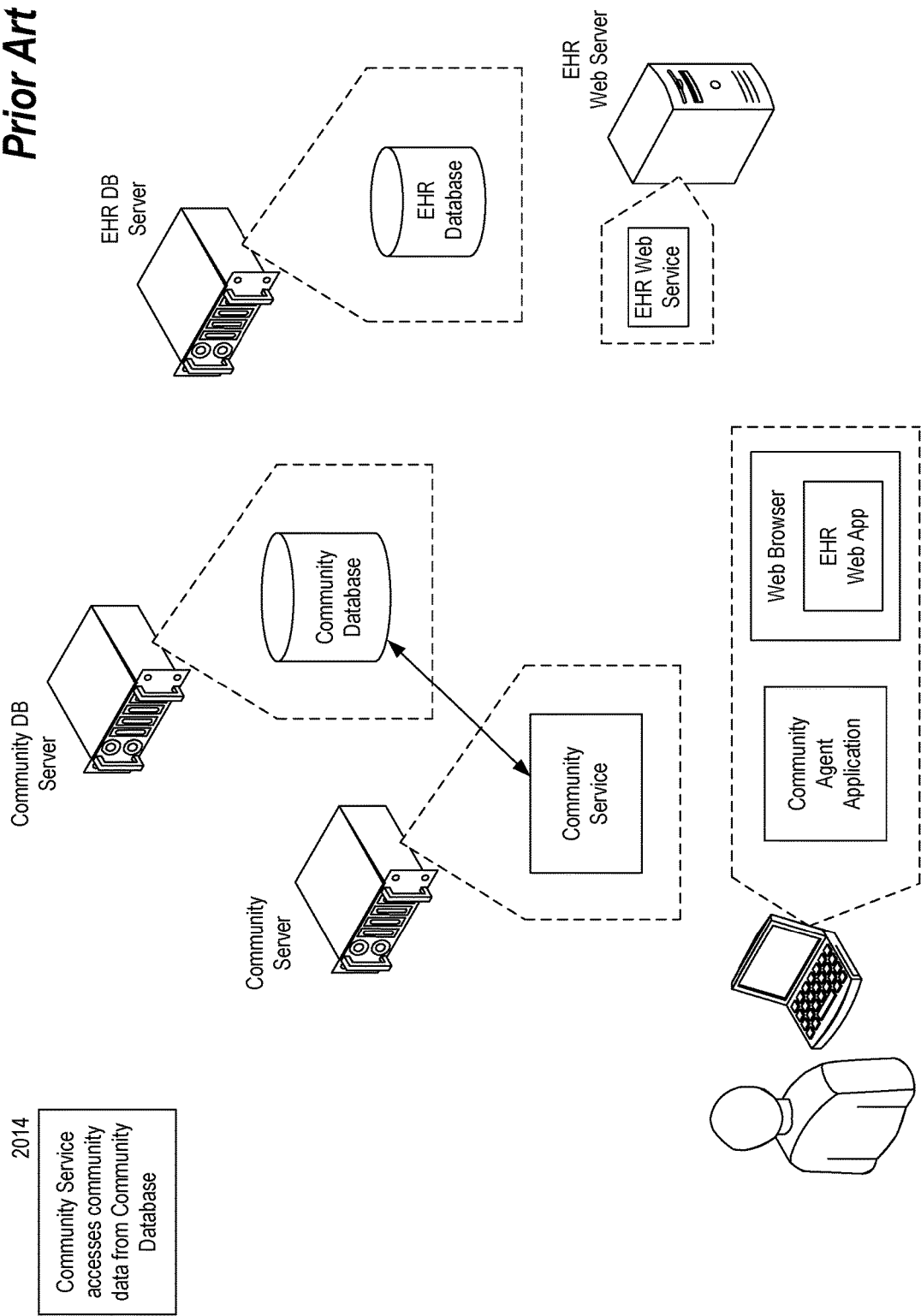
Figure 11:
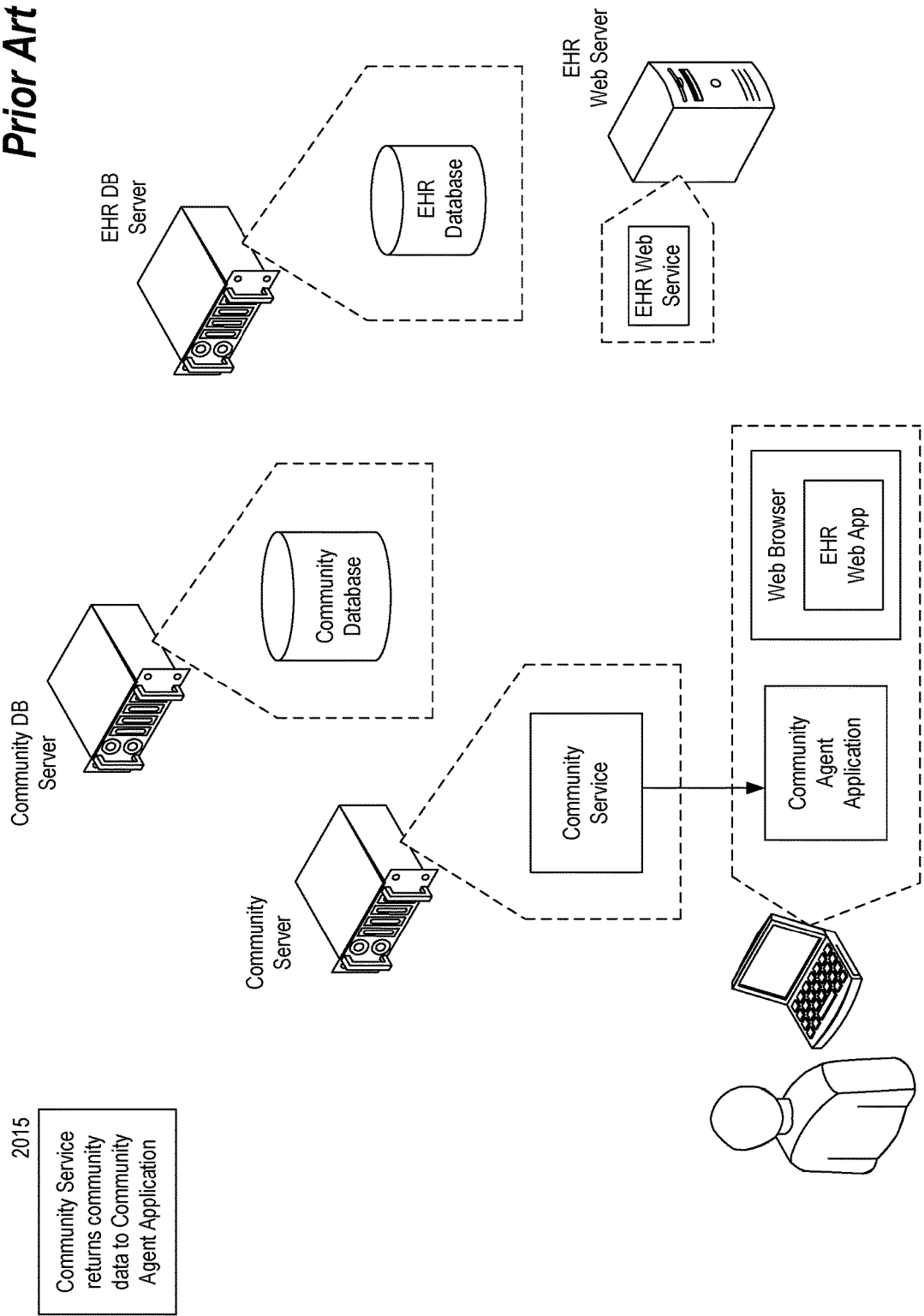
Figure 16:
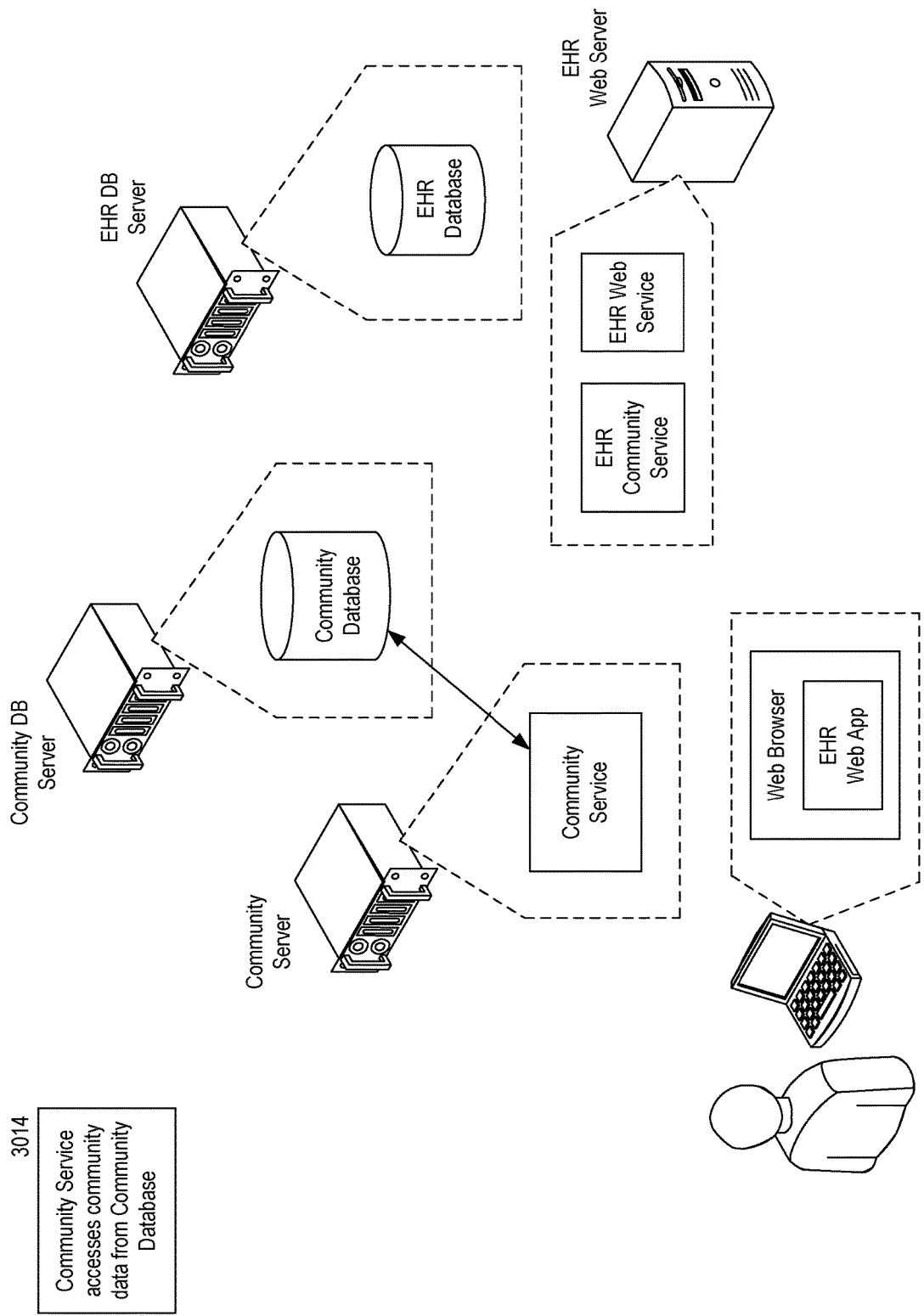
Figure 17:
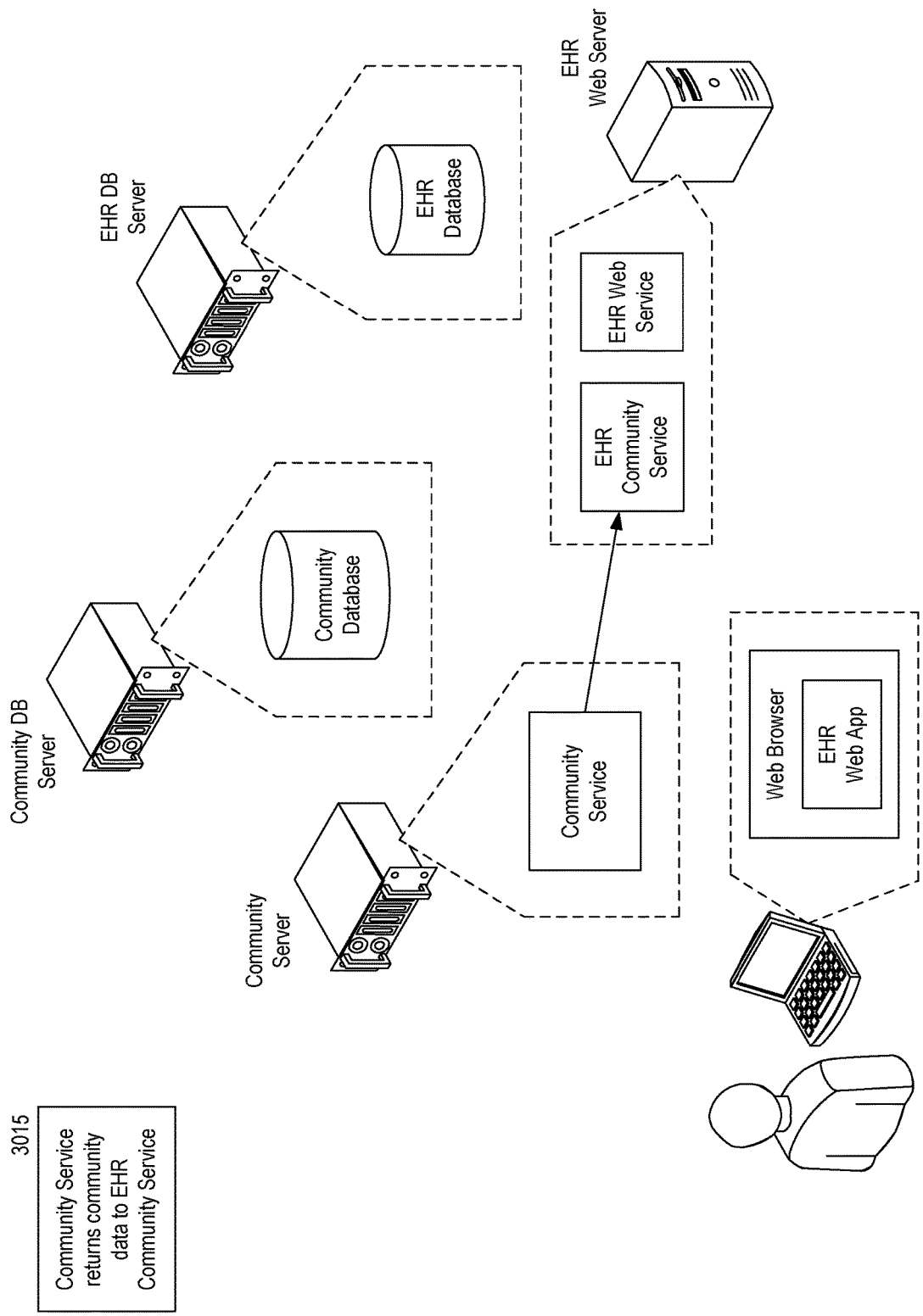

At step 3014, the community service accesses community data for the patient from a community data store or database, which may be co-located with the community service or may be remote, as illustrated in FIG. 16. Alternatively, the Community Service accesses the community data from a Community Database at a Community DB Server, as illustrated for example in FIG. 10. In either case, Alternatively, the Community Service accesses the community data from a Community Database at a Community DB Server, as illustrated for example in FIG. 10. In either case, at step 3015, the community service returns community data to the EHR community service, as illustrated in FIG. 17.

In accordance with one or more preferred implementations, the community service may filter out some information so that it will not be returned to the EHR community service. For example, the community service may filter out data items in a non-active status. In accordance with at least some implementations, such filtering may not occur. In accordance with one or more preferred implementations, such filtering may be optional and utilized or not based on an indication contained in a call to the community service.

In accordance with one or more preferred implementations, the EHR community service itself may be configured to provide EHR data for inclusion in community data. In this event, it is possible that when the community service accesses community data to return to the EHR community service, it accesses data items that were originally provided by the EHR community service. In accordance with one or more preferred implementations, the community service is configured to filter out data items previously received from the EHR community service in addition to data items found to be semantically equivalent to data items previously received from the EHR community service. In accordance with at least some implementations, such filtering does not occur, especially where filtering by the EHR community service is deemed to be more comprehensive or trustworthy to that done by the community service. In accordance with one or more preferred implementations, such filtering may be optional and utilized or not based on an indication contained in a call to the community service.

Figure 18:
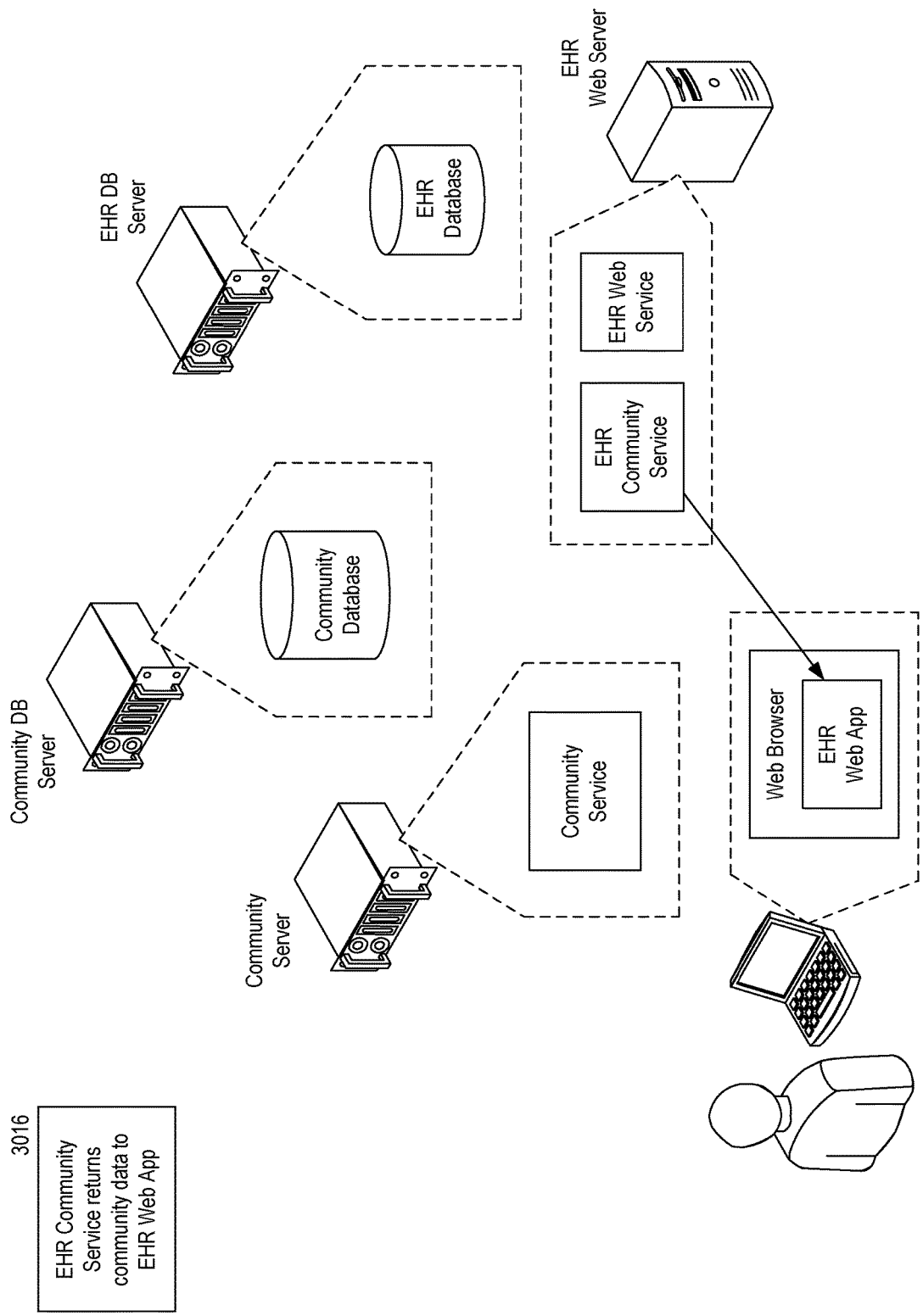

At step 3016, the EHR community service returns community data to the EHR web app, as illustrated in FIG. 18.

Figure 19:
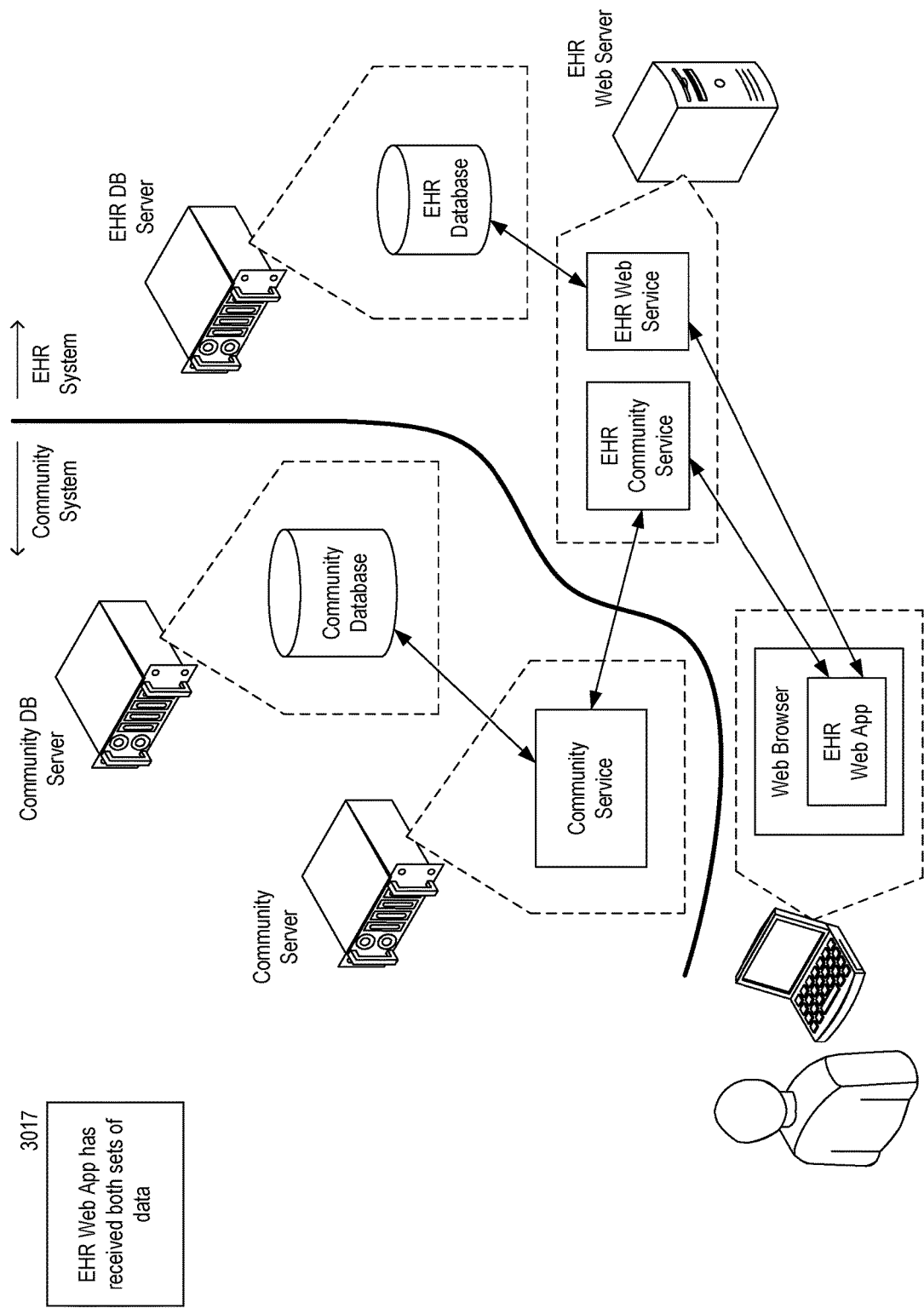

FIG. 19 illustrates the data communication pathways utilized during these steps of the methodology.

Once the EHR web app has received native data for the patient from the EHR database and has received community data for the patient from the community database, the EHR web app is ready to process the received sets of data, as signified at step 3017.

Notably, it is possible that when the EHR web app retrieves community data, it retrieves one or more duplicate data items that are already present natively in the EHR web app, e.g. a duplicate entry regarding a particular medication. Accordingly, in processing the retrieved community and native data, the EHR web app preferably screens the community data to identify data items in the community data which represent a duplicate of a native data item, as exemplified by step 3018 illustrated in FIG. 20. In accordance with one or more preferred implementations, the EHR web app preferably identifies a data item as a duplicate, a potential duplicate, or not a duplicate.

In accordance with one or more preferred implementations, a data item may be identified as a duplicate based on one or more identifiers, or based on a semantic duplicate check.

For example, a community data item may be identified as a duplicate of a native data item if a source system ID for the items match, indicating they came from the same source system, and if a source system item ID for the items match, indicating that they had the same specific ID in that source system.

Additionally, a community data item may be identified as a duplicate of a native data item based on a semantic or other comparison of data for the two data items (e.g. a comparison of data values for the two items determines that the items have identical data values for all (or all relevant) data fields). For example, a community problem data item might be determined to be a duplicate of an existing native problem data item if the two items have the same ICD code and diagnosis date (although it will be appreciated that this is a simplistic example and additional comparisons may be utilized). As another example, in a medication data item context, a community medication data item might be determined to be a duplicate based on comparison of a medication name (with brand/trade names, generic names, and chemical names corresponding to one another potentially or optionally being considered to match), strength, dosage form, code (e.g. RxNorm code), status, and date.

Additionally, in accordance with one or more preferred implementations, a community data item may be identified as a potential duplicate of a native data item. For example, a community problem data item might be determined to be a potential duplicate of an existing native problem data item if the two items have the same ICD code, but do not have the same diagnosis date. As another example, returning to the context of medication data items just discussed, a community medication data item might be determined to be a potential duplicate of an existing native medication data item if only some of the properties noted in the prior discussion match.

Figure 20:
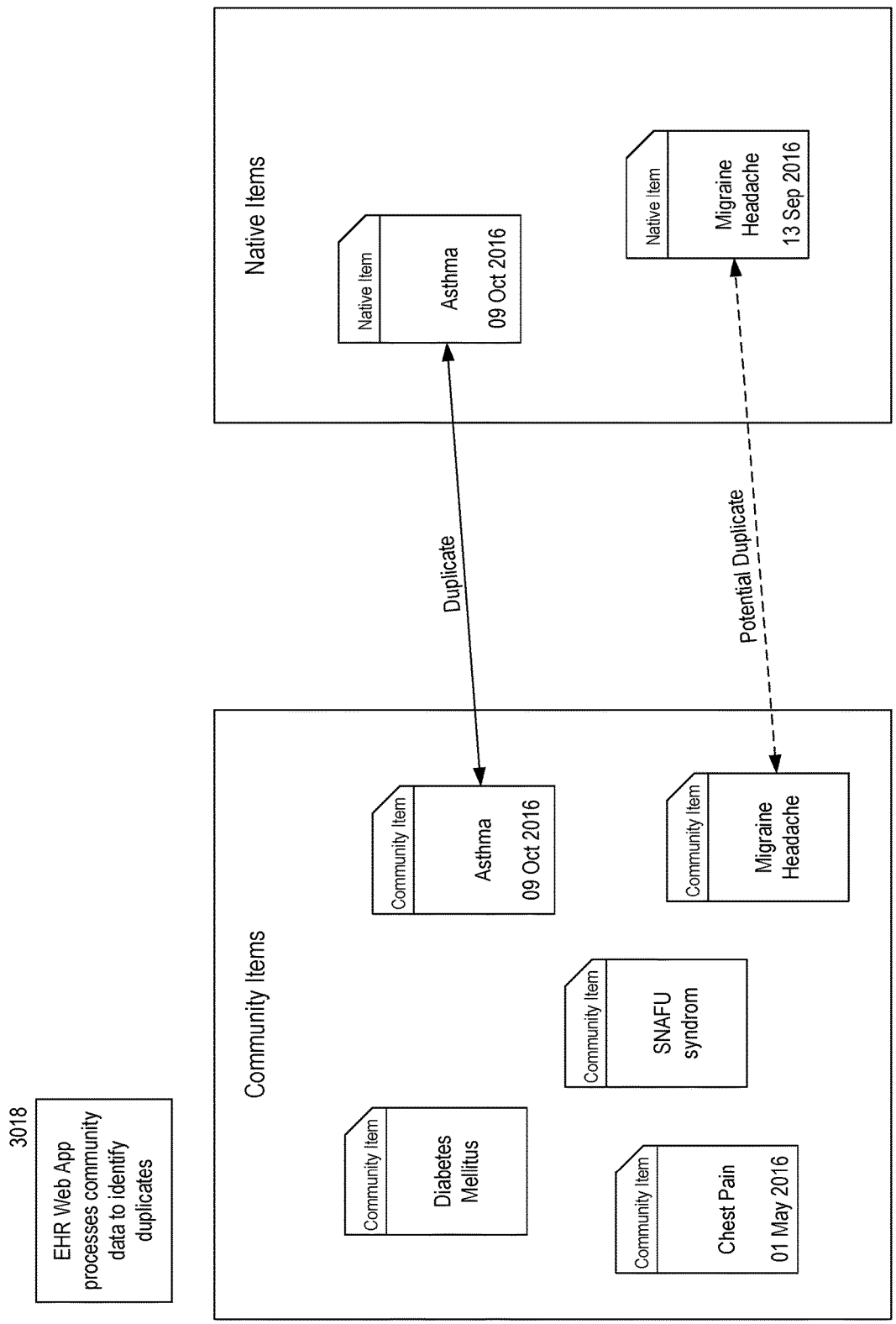

Returning to the example of FIG. 20, the asthma problem community data item having a last assessed date of Oct. 9, 2016 is determined to be a duplicate of the asthma problem native data item having a last assessed date of Oct. 9, 2016, while the migraine headache problem community data item is determined to only be a potential duplicate of the migraine headache problem native data item because the items do not have the same last assessed date.

Figure 21:
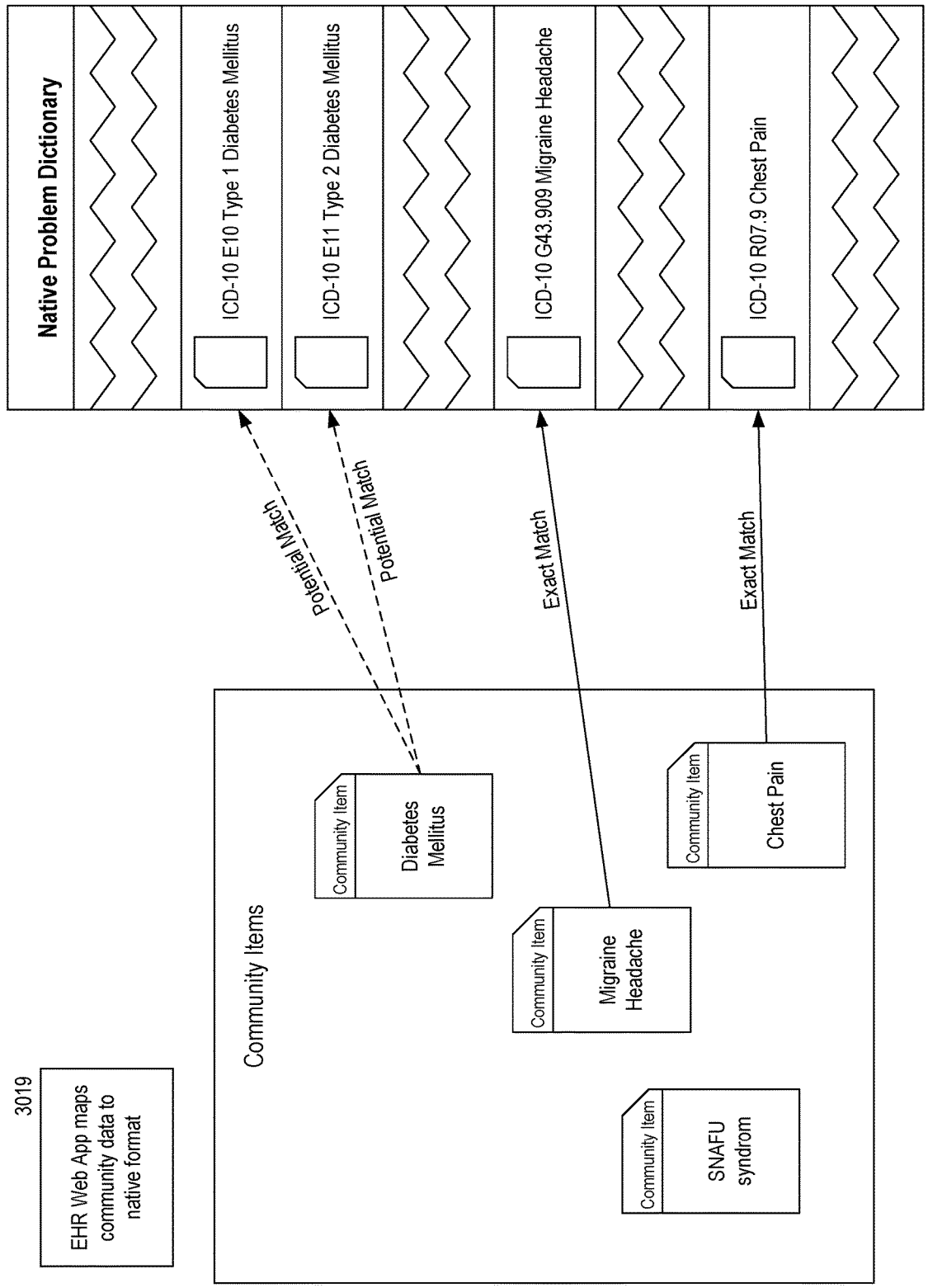

The EHR web app preferably further processes the retrieved community data and attempts to map community data items to a native format by matching community data items to entries in one or more native clinical dictionaries (e.g. a medication list), as exemplified by step 3019 illustrated in FIG. 21. As discussed in more detail hereinbelow, in accordance with one or more preferred implementations, the EHR web app preferably identifies a community data item as an exact match to one or more entries in a clinical dictionary, a near match to one or more entries in a clinical dictionary, or identifies that there was no match.

In accordance with one or more preferred implementations, attempting to match a community data item to an entry in a clinical dictionary comprises comprising a code system/value in the community data item (such as an ICD-10 code for a problem community data item) to values in the clinical dictionary (such as ICD-10 codes for problems in a problem clinical dictionary).

In accordance with one or more preferred implementations, a community data item may be identified as a potential match if a code system/value for a community data item is associated with or corresponds to more than one entry in a clinical dictionary. For example, if a community problem data item uses an ICD-9 code for Diabetes Mellitus, and a problem clinical dictionary (e.g. one based on ICD-10 codes) includes a first entry for Diabetes Mellitus Type 1 and a second entry for Diabetes Mellitus Type 2, both of which are associated with the ICD-9 code for Diabetes Mellitus, then the system may identify the community data item as a potential match to both entries.

Additionally, in accordance with one or more preferred implementations, a community data item may be identified as a potential match based on a semantic or other comparison of data in a community item to a clinical dictionary. For example, a community problem data item having a data value of "Diabetes Mellitus" for a field or property may be identified as a potential match to one or more entries in a problem clinical dictionary.

Returning to the example of FIG. 21, the migraine headache problem community data item has been identified as an exact match to the ICD-10 G43.909 Migraine Headache dictionary entry, the chest pain problem community data item has been identified as an exact match to the ICD-10 R07.9 Chest Pain dictionary entry, and the diabetes mellitus problem community data item has been identified as a potential match to both the ICD-10 E10 Type 1 Diabetes Mellitus dictionary entry, and the ICD-10 E11 Type 2 Diabetes Mellitus dictionary entry.

Notably, because the asthma problem community data item was already determined to be a duplicate of an existing native problem data item, there is no need to try to map it to the native problem dictionary. In accordance with one or more preferred implementations, such mapping may occur anyway, however, or may occur prior to duplicate checking. It will be appreciated that although these processing steps are illustrated in a particular order, this order could be reversed and/or these steps could be combined.

Figure 22:

Following this processing, at step 3020, the EHR web app displays information for the patient based on both the returned native data and the returned community data, as illustrated in FIG. 22.

As the asthma problem community data item was determined to be a duplicate of the existing asthma problem native data item, only one asthma problem is displayed. However, because the migraine headache problem community data item was determined to be a potential duplicate of the migraine headache native data item, information for both of these data items is displayed in the interface, with information for the migraine headache problem community data item being displayed under a "Potential Duplicates" sub-heading to indicate that it is a potential duplicate.

In accordance with one or more preferred implementations, data items that are potential duplicates have a flag indicating such. In accordance with one or more preferred implementations, display of potential duplicates can be toggled on or off via use of a user interface element such as a toggleable icon, as illustrated in FIG. 23.

Figure 24:

In accordance with one or more preferred implementations, an interface of an EHR web app displays a user interface element such as an icon for each community data item which indicates whether an attempt to map the community data item resulted in an exact match, one or more possible matches, or no matches. The exemplary interface of FIG. 22 includes exemplary such icons. For example, the interface includes an icon associated with the chest pain problem community data item which indicates that this data item is an exact match to an entry in the native problem clinical dictionary, as illustrated in FIG. 24.

In accordance with one or more preferred implementations, a user can import a community data item into the native application, which serves to convert it into a native data item (which may be implemented by changing properties of the data item and/or creating a new native data item).

From the exemplary interface of FIG. 22, this can be accomplished in a number of ways. For a community data item that has been determined to be an exact match, such as the illustrated chest pain problem community data item, a user can interact with the listing of the data item and select an import option from a context menu, or can interact with the displayed icon indicating that the community data item is an exact match. In any of these events, because the chest pain problem community data item is an exact match, the data item can automatically be converted to a native data item, as illustrated in FIG. 25 (although in accordance with one or more preferred implementations a user might be prompted to furnish additional information regarding the data item to fill in data fields or properties for the native application). Additionally, in accordance with one or more preferred implementations, an interface might include a user interface element configured to allow a user to batch import all of the displayed community data items that have been determined to be an exact match. FIG. 22 illustrates such a user interface element, where the same icon utilized to indicate an exact match is present in an upper right corner of a panel of the interface and is configured to effect such a batch import.

In accordance with one or more preferred implementations, a community item that has been imported into an EHR web app as a native item includes one or more fields or properties which indicate that the source of the item is community data. In accordance with one or more preferred implementations, one or more fields or properties list an original source of the community data.

In accordance with one or more preferred implementations, an EHR web app may be configured to keep track of user changes as work-in-progress (WIP), and not make such changes final (e.g. save them to a data store such that they will be available to other users) until the user commits such changes. In accordance with one or more preferred implementations, importing a community data item causes the item to immediately be imported as work-in-progress, and henceforth the item is treated as a native data item.

In accordance with one or more preferred implementations, upon importing a community data item, a clone of the original community data item or the original community data item itself is added to an in-memory cache which can be utilized if the WIP changes are rolled back by the user. Alternatively or additionally, the original community data in its entirety may be cached for use in this manner.

In accordance with one or more preferred implementations, once a user chooses to commit work-in-progress changes (e.g. by interacting with a "Commit" button), the changes will be saved to a data store and any community data items that were imported as part of that work-in-progress will be committed as native data items.

It is not quite as easy to import a community data item that has only been determined to be a potential match. To import a community data item that has been determined to be a potential match, a user can interact with the listing of the data item and select an import option from a context menu, or can interact with the displayed icon indicating that the community data item is a potential match.

In either event, an interface is displayed which displays the potential matches and allows the user to select one to import, as illustrated in FIG. 26. For example, if the user selects the displayed listing for "E10 Type 1 Diabetes Mellitus", the community data item will be imported as a native data item, as illustrated in FIG. 27. Alternatively, if the user is not satisfied with any of the displayed potential matches, the user can open a search interface and search (e.g. search a clinical dictionary) for a match.

Figure 28:
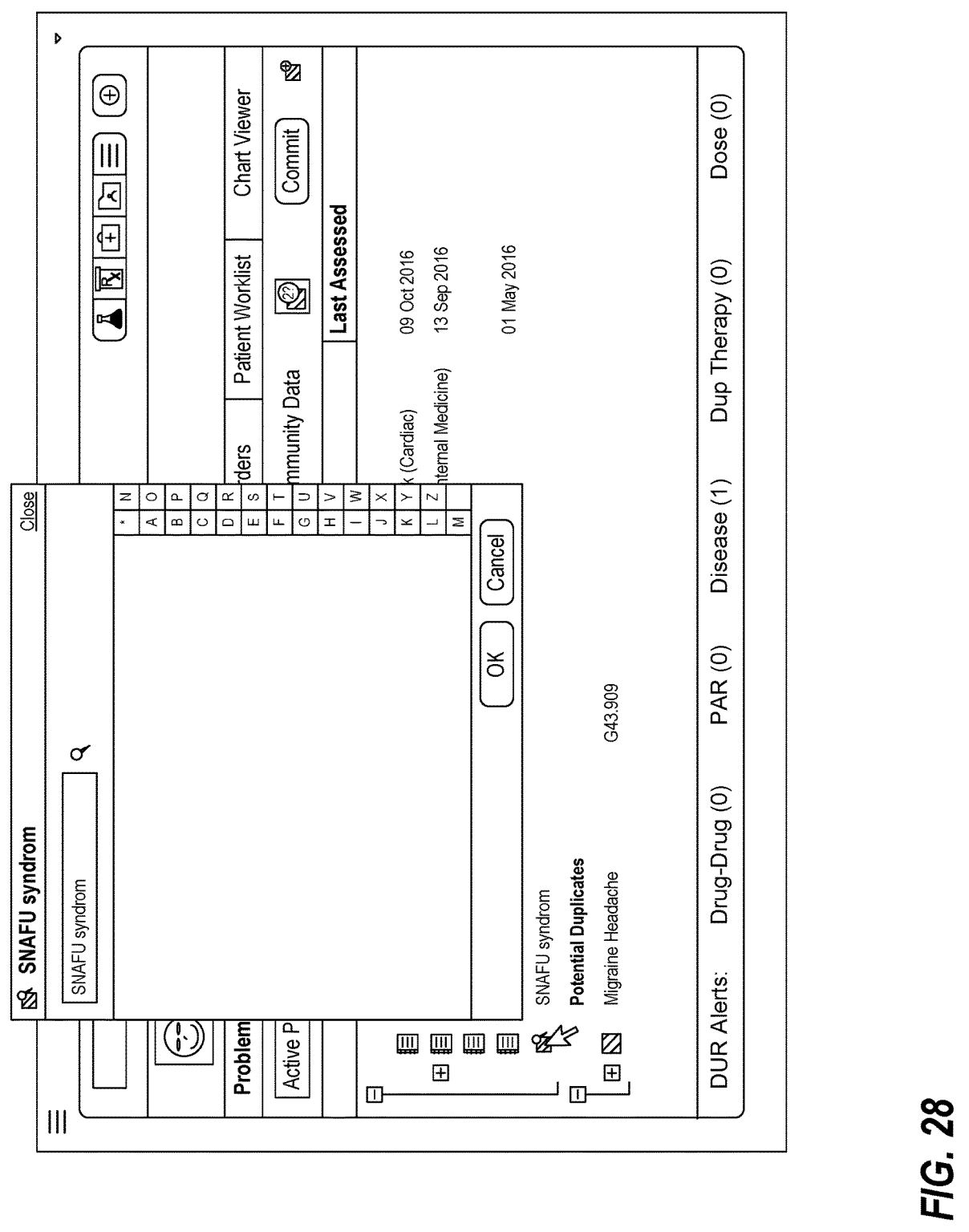

Similarly, in order to import a community data item which has not been automatically determined to be a match or potential match, a user must utilize a search interface to search for a match. To access this search interface for a community data item that has not determined to be a match or potential match, a user can interact with the listing of the data item and select an import option from a context menu, or can interact with the displayed icon indicating that the community data item has not been determined to be a match or potential match. FIG. 28 illustrates an exemplary search interface for the "SNAFU syndrom" community data item. In accordance with one or more preferred implementations, the search interface is preferably prepopulated with information from the community data item (e.g. the text string "SNAFU syndrom") as a search criteria and the corresponding results (although in this case no results were found for "SNAFU syndrom").

It will be appreciated that EHR web apps are commonly set up to perform Drug Utilization Review (DUR) checking to determine, for example, whether two medications in a patient's record might have a negative interaction with one another, or whether a medication in a patient's record is contraindicated based on a problem or condition in the patient's record. Similar checking can be performed for patient allergies and patient immunizations.

Figure 29:
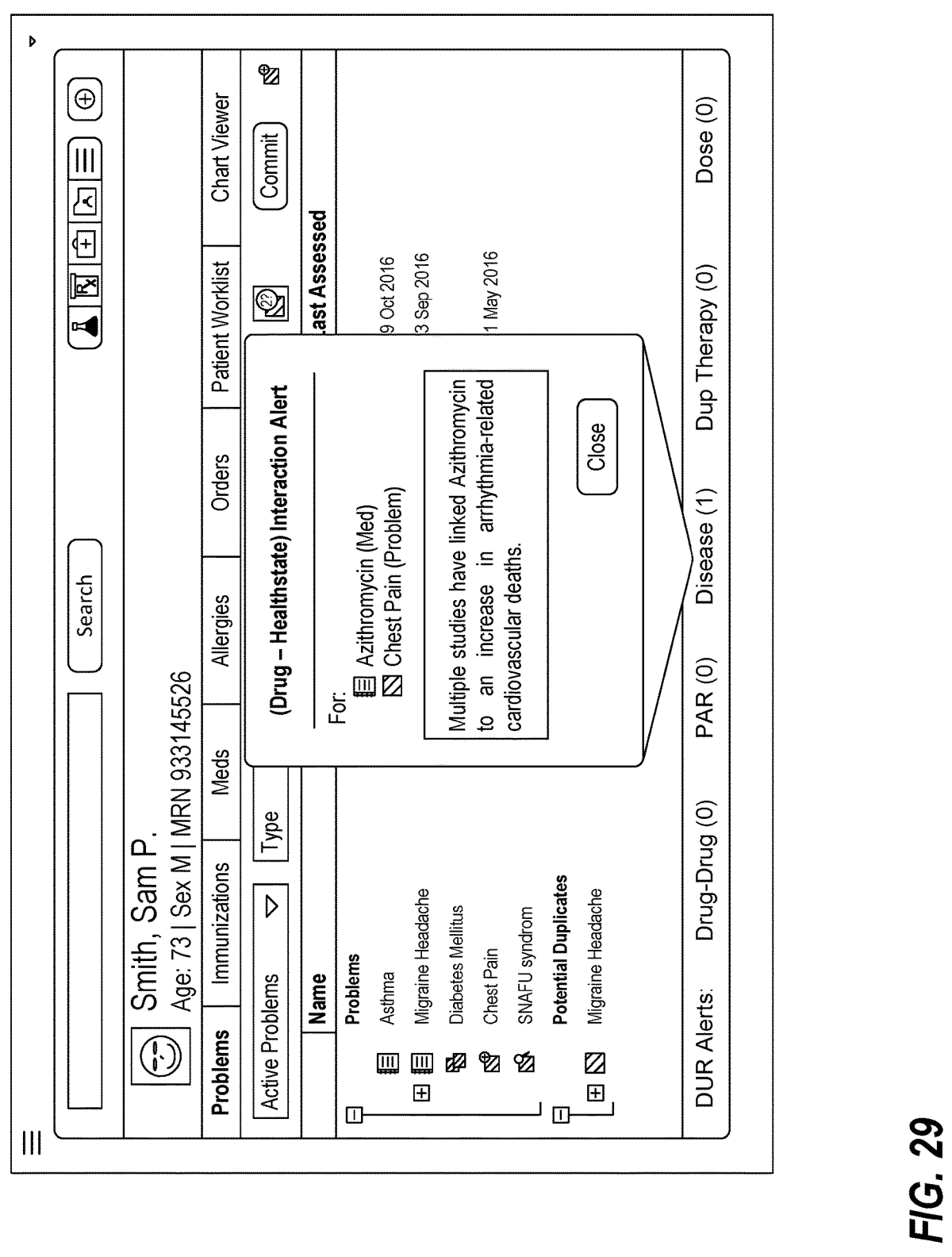

In accordance with one or more preferred implementations, DUR checking utilizes community data. For example, when community data was loaded as illustrated in FIG. 22, DUR checking flagged that a medication in the patient's record is contraindicated based on a community problem. A user can click on the relevant DUR banner to display more information regarding this, as illustrated in FIG. 29.

In accordance with one or more preferred implementations, users can specify, for different permutations of DUR alerts, whether community data is utilized in DUR checking. In accordance with one or more preferred implementations, only community data items for which an exact match has been identified are utilized in DUR checking, while in accordance with one or more preferred implementations, other community data items may be utilized as well.

Figure 30:

It will be appreciated that a user may occasionally find him or herself presented with a community data item that he or she does not wish to continue to see in a patient's record. In accordance with one or more preferred implementations, a user is able to suppress a community data item to prevent future display of that community data item. In accordance with one or more preferred implementations, suppression of a community data item is user-specific, while in accordance with one or more preferred implementations suppression of a community data item may effect viewing of the item by other users as well. FIGS. 30-31 illustrate suppression of the "SNAFU syndrom" community data item.

In accordance with one or more preferred implementations, suppressed items can subsequently be un-suppressed by a user utilizing one or more user interface elements.

In accordance with one or more preferred implementations, suppressed items are not utilized for DUR checking.

In accordance with one or more preferred implementations, implementation of suppression functionality is provided by storing a listing of community data items (e.g. in a database storing a community source ID and a community source item ID) which are to be suppressed and comparing loaded community data items against that listing. In accordance with one or more preferred implementations, implementation of suppression functionality is provided utilizing a flag which indicates whether a particular community data item is suppressed. In accordance with one or more preferred implementations, a listing of suppressed community data items is utilized to set such a flag for newly loaded community data items.

In accordance with one or more alternative implementations, implementation of suppression functionality is provided by removing a suppressed item from an item collection representing community data items and adding it to a collection of suppressed items. In accordance with one or more preferred implementations, this allows the collection representing community data items to be utilized (e.g. for Drug Utilization Review (DUR) checking) without utilizing suppressed items, and further allows a user interface component to not have to handle additional checking for suppressed items in the collection.

In accordance with one or more preferred implementations, duplicate checking may include duplicate checking of or against suppressed items.

In accordance with one or more preferred implementations, suppressed items may be characterized as rejected items.

In accordance with one or more preferred implementations, audit data is saved for user actions with respect to community data. In accordance with one or more preferred implementations, audit data is saved for retrieve events, import events, view events, toggle events for a show community data interface element, suppress events, and unsuppress events.

In accordance with one or more preferred implementations, an interface of an EHR web app includes a user interface element configured to allow a user to toggle whether community data is to be shown. In accordance with one or more preferred implementations, if this setting is toggled on, then community data is automatically loaded for a patient upon a context change to that patient. In accordance with one or more preferred implementations, however, if this setting is toggled off, then community data is not loaded upon a context change to a new patient, and is only loaded upon toggling of this setting to on.

In accordance with one or more preferred implementations, one or more settings related to showing community data can be configured at the enterprise, organizational, or user level.

In accordance with one or more preferred implementations, when an EHR web app loads a record for a particular patient, the EHR web app determines whether to retrieve community data for that patient. In accordance with one or more preferred implementations, community data is cached, either locally or at a server (e.g. at the EHR web server or EHR DB server), and new data is only retrieved utilizing a community service if the relevant community data is not cached for a particular patient, or if the last retrieval time for the relevant community data for that patient was more than a set time ago (e.g. twenty four hours). In accordance with one or more preferred implementations, this time period is user configurable. In accordance with one or more preferred implementations, this time period is only configurable by a system administrator.

In accordance with one or more preferred implementations, an EHR web app includes clinical decision support (CDS) functionality, and community data items can be utilized as triggers for CDS recommendations. In accordance with one or more preferred implementations, only community data items for which an exact match has been identified are utilized as triggers for CDS recommendations, while in accordance with one or more preferred implementations, other community data items may be utilized as well.

Exemplary methodologies have been described herein, and illustrated in the figures, with respect to accessing and utilizing community data for problems or medications associated with a patient. It will be appreciated that these are only example of the types of community data that can be utilized in such methodologies. As noted hereinabove, such methodologies can involve receiving a virtual patient object (VPO) including community data for a patient related to all sorts of different domains, including problems, allergies, medications, immunizations, orders, clinical documentation, results, etc. In accordance with one or more preferred implementations, community data for one or more of these domains is utilized in accordance with methodologies described herein.

For example, with respect to immunizations, community immunization data may be retrieved and special duplicate rules based on Center for Disease Control (CDC) guidelines may be utilized to determine whether an immunization is a duplicate. In particular, if the name, CVX code (and possibly the MVX code as well), and administration date for a community immunization data item match the same values for a native immunization data item, then the community immunization data item will be considered an exact duplicate. If, on the other hand, the date does not match, then, based on CDC guidelines, the two items will only be considered a potential match if the two dates are within twenty three days of one another. Otherwise, the two items will not be identified as even a potential match.

As another example, with respect to allergies, in accordance with one or more preferred implementations, community allergy data may be utilized to display an alert, as illustrated in FIG. 32.

In accordance with one or more preferred implementation, when one or more particular types of community data items are to be imported (e.g. a community data item with a potential match or no match), such as a community immunization data item, a DUR check is performed prior to importing. In accordance with one or more preferred implementations, any possible DUR alerts must be resolved prior to importing.

In accordance with one or more preferred implementations, an EHR web app is configured to allow a user to link two data items, e.g. link an immunization to a particular problem. In accordance with one or more preferred implementations, such linking can only be performed for a community data item once that community data item has been imported.

In accordance with one or more preferred implementations, potentially duplicate community data items will not be utilized during DUR, will not appear in notes, and/or will not be included in outbound feeds (e.g. communications to a community service).

In accordance with one or more preferred implementations, a community service may return community data for a patient (e.g. in the form of a VPO) which includes optional data (e.g. fields or properties) that are not required in an EHR web app. In accordance with one or more preferred implementations, a community service may even return data that is not normally tracked in the EHR web app. In accordance with one or more preferred implementations, an EHR web app may handle such extra information in a variety of different ways.

For example, fields from community data which do not correspond to any field in an EHR web app may be mapped to a related field, or displayed in a closely related field or in an area for miscellaneous data.

In accordance with one or more preferred implementations, run-time duplicate identification and mapping/matching is carried out.

In accordance with one or more preferred implementations, an EHR web app is configured to cache data items (native and/or community data items) locally at a user device. In accordance with one or more preferred implementations, an EHR web app is configured to cache data items (native and/or community data items) at a server (e.g. at an EHR web server).

As described hereinabove, in accordance with one or more preferred implementations, an EHR web app is configured to perform duplicate identification and mapping/matching locally. In accordance with one or more preferred implementations, however, an EHR web app is configured to perform duplicate identification and mapping/matching at a server (e.g. at an EHR web server).

As stated above, it should be appreciated that such EHR web app represents an EHR application, which need no be in the form of a web app per se. Indeed, in accordance with the invention, an EHR application could be in the form of a standalone windows application or other program, including for example, and not by way of limitation, a thin-client application or a cloud application.

Various methodologies are described herein utilizing various coding schemes. It will be appreciated that methodologies disclosed herein could alternatively or additionally utilize various other coding schemes. For example, methodologies in accordance with one or more preferred implementations may utilize Systematized Nomenclature of Medicine (SNOMED) code, Logical Observation Identifiers Names and Codes (LOINC), National Drug Code (NDC), ICD-9 codes, ICD-9-CM codes, ICD-10 codes, and/or RxNorm codes.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method for facilitating integration of patient electronic healthcare record information from a community aggregator with electronic healthcare record information native to an electronic healthcare record (ERR) application, the method comprising:
    (a) receiving, via a first interface of an ERR web app loaded in a web browser running on a user device, first user input corresponding to selection of a patient effecting a new patient context;
    (b) in response thereto,
        (i) effecting a first asynchronous flow involving
            (A) communicating, from the ERR web app to an ERR web service at an ERR web server, a request for native patient data for the patient,
            (B) accessing, by the ERR web service, native patient data for the patient,
            (C) returning, from the ERR web service to the ERR web app, the accessed native patient data, and
        (ii) effecting a second asynchronous flow involving
            (A) communicating, from the ERR web app to an ERR community service at the ERR web server, a request for community patient data for the patient,
            (B) communicating, from the ERR community service to a community service at a community server, a request for community patient data for the patient,
            (C) accessing, by the community service, community patient data for the patient,
            (D) returning, from the community service to the ERR community service, the accessed community patient data,
            (E) returning, from the ERR community service to the ERR web app, the accessed community patient data,
        (iii) in response to completion of the first asynchronous flow and the second asynchronous flow, processing the accessed community patient data by
            (A) for each community data item of a plurality of community data items in the accessed community patient data,
                (1) comparing the community data item to native data items in the accessed native patient data in order, and
                (2) based on the comparison, identifying the community data item as
                    (I) a duplicate,
                    (II) a potential duplicate, or
                    (III) not a duplicate, and
            (B) for each community data item of the plurality of community data items which was not identified as a duplicate,
                (1) comparing the community data item to entries in one or more native clinical dictionaries, and
                (2) based on the comparison, identifying the community data item as
                    (I) an exact match to a clinical dictionary entry,
                    (II) a potential match to one or more clinical dictionary entries, or
                    (III) not matched to any clinical dictionary entry, and
        (iv) displaying, in a second interface of the ERR web app,
            (A) a listing for each of
                (1) one or more native data items from the accessed native patient,
                (2) one or more community data items that were identified to be a definite match to a clinical dictionary entry,
                (3) one or more community data items that were identified to be a potential match to one or more clinical dictionary entries,
                (4) one or more community data items that were identified as not being matched to any clinical dictionary entry, and
                (5) one or more community data items that were identified as a potential duplicate,
                (6) wherein there is no listing displayed for any community data item identified as a duplicate,
            (B) for each listing for one of the community data items that was identified to be a definite match to a clinical dictionary entry, a visual indication that the listing is for a community data item that was identified to be a definite match,
            (C) for each listing for one of the community data items that was identified to be a potential match to a clinical dictionary entry, a visual indication that the listing is for a community data item that was identified to be a potential match, (D) for each listing for one of the community data items that was identified as not being matched to any clinical dictionary entry, a visual indication that the listing is for a community data item that was identified that was identified as not being matched to any clinical dictionary entry, (E) one or more visual indications that the one or more community data items that were identified as a potential duplicate are potential duplicates, (c) receiving, via the second interface of the ERR web app, second user input corresponding to interaction with the listing for a first community data item, the first community data item being one of the community data items that was identified to be a definite match to a clinical dictionary entry, and the interaction representing an indication to import the first community data item in the ERR web app;

(d) automatically converting, in response to the second user input, the first community data item to a first community native data item based on the clinical dictionary entry it was identified to be a definite match to;

(e) receiving, via the second interface of the ERR web app, third user input corresponding to interaction with the listing for a second community data item, the second community data item being one of the community data items that was identified to be a potential match to one or more clinical dictionary entries, and the interaction representing an indication to import the second community data item in the ERR web app;

(f) displaying, in response to the third user input, a third interface of the ERR web app which includes a listing for each of the clinical dictionary entries that the second community data item was identified to be a potential match to;

(g) receiving, via the third interface of the ERR web app, fourth user input corresponding to selection of one of the listed clinical dictionary entries; and (h) automatically converting, based on the fourth user input, the second community data item to a second community native data item based on the selected clinical dictionary entry.

2. The method of claim 1, wherein communicating, from the ERR community service to a community service at a community server comprises a request for community patient data for the patient comprises making an API call.

3. The method of claim 1, wherein communicating, from the ERR community service to a community service at a community server comprises a request for community patient data for the patient comprises accessing a URL.

4. The method of claim 1, wherein communicating, from the ERR community service to a community service at a community server comprises a request for community patient data for the patient comprises communicating a request including a parameter specifying one or more filter options.

5. The method of claim 1, wherein returning, from the community service to the ERR community service, the accessed community patient data comprises returning a virtual patient object.

6. The method of claim 1, wherein the method further comprises receiving, from the user, user input corresponding to an indication to suppress one or the displayed community data items.

7. The method of claim 6, wherein the method further comprises updating the second interface of the ERR web app to no longer display the suppressed community data item.

8. The method of claim 6, wherein the method further comprises storing, in a suppression data table, a source identifier and a source item identifier for the community item to be suppressed.

9. The method of claim 8, wherein the method further comprises subsequently comparing loaded community items to information stored in the suppression data table to determine whether to suppress the loaded community items.

10. The method of claim 1, wherein the user device comprises a laptop.

11. The method of claim 1, wherein the user device comprises a desktop computer.

12. The method of claim 1, wherein the user device comprises a tablet.

13. The method of claim 1, wherein the user device comprises a phone.

14. The method of claim 1, wherein the user device comprises a smart appliance.

15. A method for facilitating integration of patient electronic healthcare record information from a community aggregator with electronic healthcare record information native to an electronic healthcare record (ERR) application, the method comprising:

(a) receiving, via a first interface of an ERR web app loaded in a web browser running on a user device, first user input corresponding to selection of a patient effecting a new patient context;

(b) in response thereto,
  (i) effecting a first asynchronous flow involving
    (A) communicating, from the ERR web app to an ERR web service at an ERR web server, a request for native patient data for the patient,
    (B) accessing, by the ERR web service, native patient data for the patient,
  (ii) effecting a second asynchronous flow involving
    (A) communicating, from the ERR web app to an ERR community service at the ERR web server, a request for community patient data for the patient,
    (B) communicating, from the ERR community service to a community service at a community server, a request for community patient data for the patient,
    (C) accessing, by the community service, community patient data for the patient,
    (D) returning, from the community service to the ERR community service, the accessed community patient data,
  (iii) in response to completion of the first asynchronous flow and the second asynchronous flow, processing the accessed community patient data at the ERR web server by
    (A) for each community data item of a plurality of community data items in the accessed community patient data,
      (1) comparing the community data item to native data items in the accessed native patient data in order, and
      (2) based on the comparison, identifying the community data item as
        (I) a duplicate,
        (II) a potential duplicate, or
        (III) not a duplicate, and
    (B) for each community data item of the plurality of community data items which was not identified as a duplicate,
      (1) comparing the community data item to entries in one or more native clinical dictionaries, and (2) based on the comparison, identifying the community data item as
(I) an exact match to a clinical dictionary entry,
(II) a potential match to one or more clinical dictionary entries, or
(III) not matched to any clinical dictionary entry, and
(iv) displaying, in a second interface of the ERR web app,
(A) a listing for each of
(1) one or more native data items from the accessed native patient data,
(2) one or more community data items that were identified to be a definite match to a clinical dictionary entry,
(3) one or more community data items that were identified to be a potential match to one or more clinical dictionary entries,
(4) one or more community data items that were identified as not being matched to any clinical dictionary entry, and
(5) one or more community data items that were identified as a potential duplicate,
(6) wherein there is no listing displayed for any community data item identified as a duplicate,
(B) for each listing for one of the community data items that was identified to be a definite match to a clinical dictionary entry, a visual indication that the listing is for a community data item that was identified to be a definite match,
(C) for each listing for one of the community data items that was identified to be a potential match to a clinical dictionary entry, a visual indication that the listing is for a community data item that was identified to be a potential match,
(D) for each listing for one of the community data items that was identified as not being matched to any clinical dictionary entry, a visual indication that the listing is for a community data item that was identified that was identified as not being matched to any clinical dictionary entry,
(E) one or more visual indications that the one or more community data items that were identified as a potential duplicate are potential duplicates,
(c) receiving, via the second interface of the ERR web app, second user input corresponding to interaction with the listing for a first community data item, the first community data item being one of the community data items that was identified to be a definite match to a clinical dictionary entry, and the interaction representing an indication to import the first community data item in the ERR web app;
(d) automatically converting, in response to the second user input, the first community data item to a first community native data item based on the clinical dictionary entry it was identified to be a definite match to;
(e) receiving, via the second interface of the ERR web app, third user input corresponding to interaction with the listing for a second community data item, the second community data item being one of the community data items that was identified to be a potential match to one or more clinical dictionary entries, and the interaction representing an indication to import the second community data item in the ERR web app;
(f) displaying, in response to the third user input, a third interface of the ERR web app which includes a listing for each of the clinical dictionary entries that the second community data item was identified to be a potential match to;
(g) receiving, via the third interface of the ERR web app, fourth user input corresponding to selection of one of the listed clinical dictionary entries; and
(h) automatically converting, based on the fourth user input, the second community data item to a second community native data item based on the selected clinical dictionary entry.

16. A method for facilitating integration of patient electronic healthcare record information from a community aggregator with electronic healthcare record information native to an electronic healthcare record (ERR) system, the method comprising:
(a) receiving, via a first interface of an ERR application of the ERR system running on a user device, first user input corresponding to selection of a patient effecting a new patient context;
(b) in response thereto,
(i) effecting a first asynchronous flow involving
(A) communicating, from the ERR application to an ERR web service at an ERR web server, a request for native patient data for the patient,
(B) accessing, by the ERR web service, native patient data for the patient, and
(C) returning, from the ERR web service to the ERR application, the accessed native patient data, and
(ii) effecting a second asynchronous flow involving
(A) communicating, from the ERR application to an ERR community service at the ERR web server, a request for community patient data for the patient,
(B) communicating, from the ERR community service to a community service at a community server, a request for community patient data for the patient,
(C) accessing, by the community service, community patient data for the patient,
(D) returning, from the community service to the ERR community service, the accessed community patient data, and
(E) returning, from the ERR community service to the ERR application, the accessed community patient data,
(iii) in response to completion of the first asynchronous flow and the second asynchronous flow, processing the accessed community patient data by
(A) for each community data item of a plurality of community data items in the accessed community patient data,
(1) comparing the community data item to native data items in the accessed native patient data in order, and
(2) based on the comparison, identifying the community data item as
(I) a duplicate,
(II) a potential duplicate, or
(III) not a duplicate, and
(B) for each community data item of the plurality of community data items which was not identified as a duplicate,
(1) comparing the community data item to entries in one or more native clinical dictionaries, and
(2) based on the comparison, identifying the community data item as
(I) an exact match to a clinical dictionary entry, (II) a potential match to one or more clinical dictionary entries, or (III) not matched to any clinical dictionary entry, and (iv) displaying, in a second interface of the ERR application, (A) a listing for each of (1) one or more native data items from the accessed native patient, (2) one or more community data items that were identified to be a definite match to a clinical dictionary entry, (3) one or more community data items that were identified to be a potential match to one or more clinical dictionary entries, (4) one or more community data items that were identified as not being matched to any clinical dictionary entry, and (5) one or more community data items that were identified as a potential duplicate, (6) wherein there is no listing displayed for any community data item identified as a duplicate, (B) for each listing for one of the community data items that was identified to be a definite match to a clinical dictionary entry, a visual indication that the listing is for a community data item that was identified to be a definite match, (C) for each listing for one of the community data items that was identified to be a potential match to a clinical dictionary entry, a visual indication that the listing is for a community data item that was identified to be a potential match, (D) for each listing for one of the community data items that was identified as not being matched to any clinical dictionary entry, a visual indication that the listing is for a community data item that was identified as not being matched to any clinical dictionary entry, and (E) one or more visual indications that the one or more community data items that were identified as a potential duplicate are potential duplicates, (c) receiving, via the second interface of the ERR application, second user input corresponding to interaction with the listing for a first community data item, the first community data item being one of the community data items that was identified to be a definite match to a clinical dictionary entry, and the interaction representing an indication to import the first community data item in the ERR application;

(d) automatically converting, in response to the second user input, the first community data item to a first community native data item based on the clinical dictionary entry it was identified to be a definite match to;

(e) receiving, via the second interface of the ERR application, third user input corresponding to interaction with the listing for a second community data item, the second community data item being one of the community data items that was identified to be a potential match to one or more clinical dictionary entries, and the interaction representing an indication to import the second community data item in the ERR application;

(f) displaying, in response to the third user input, a third interface of the ERR application which includes a listing for each of the clinical dictionary entries that the second community data item was identified to be a potential match to;

(g) receiving, via the third interface of the ERR application, fourth user input corresponding to selection of one of the listed clinical dictionary entries; and (h) automatically converting, based on the fourth user input, the second community data item to a second community native data item based on the selected clinical dictionary entry.

17. The method of claim 16, wherein the ERR application comprises a web app.

18. The method of claim 16, wherein the ERR application comprises a cloud app.

19. The method of claim 16, wherein the ERR application comprises a desktop application.

20. The method of claim 16, wherein the ERR application comprises a thin-client application.

* * * * *